(12) United States Patent
Kato et al.

(10) Patent No.: US 9,289,411 B2
(45) Date of Patent: Mar. 22, 2016

(54) ANTI-HCV AGENT

(71) Applicant: NATIONAL UNIVERSITY CORPORATION OKAYAMA UNIVERSITY, Okayama (JP)

(72) Inventors: Nobuyuki Kato, Okayama (JP); Masanori Ikeda, Okayama (JP); Yusuke Wataya, Okayama (JP); Hye-Sook Kim, Okayama (JP); Hiroyuki Doi, Okayama (JP)

(73) Assignee: NATIONAL UNIVERSITY CORPORATION OKAYAMA UNIVERSITY, Okayama (JP)

( * ) Notice: Subject to any disclaimer, the term of this patent is extended or adjusted under 35 U.S.C. 154(b) by 23 days.

(21) Appl. No.: 14/348,565

(22) PCT Filed: Oct. 2, 2012

(86) PCT No.: PCT/JP2012/075461
§ 371 (c)(1),
(2) Date: Jul. 15, 2014

(87) PCT Pub. No.: WO2013/051531
PCT Pub. Date: Apr. 11, 2013

(65) Prior Publication Data
US 2014/0242030 A1 Aug. 28, 2014

(30) Foreign Application Priority Data
Oct. 3, 2011 (JP) .................................. 2011-219377

(51) Int. Cl.
| | |
|---|---|
| *A61K 31/335* | (2006.01) |
| *A61K 31/357* | (2006.01) |
| *A61K 38/21* | (2006.01) |
| *A61K 31/7056* | (2006.01) |
| *C07D 323/00* | (2006.01) |
| *A61K 38/13* | (2006.01) |
| *A61K 31/405* | (2006.01) |

(52) U.S. Cl.
CPC .............. *A61K 31/357* (2013.01); *A61K 31/405* (2013.01); *A61K 31/7056* (2013.01); *A61K 38/13* (2013.01); *A61K 38/21* (2013.01); *A61K 38/212* (2013.01); *C07D 323/00* (2013.01)

(58) Field of Classification Search
CPC .................................................... A61K 31/357
USPC ................................................. 514/450, 894
See application file for complete search history.

(56) References Cited

U.S. PATENT DOCUMENTS 8,927,596 B2 * 1/2015 Wataya et al. ................. 514/450

FOREIGN PATENT DOCUMENTS

| EP | 2 340 829 A1 | 7/2011 |
|---|---|---|
| JP | 2000-229965 | 8/2000 |
| JP | 2003-104967 | 4/2003 |
| JP | 2003-335774 | 11/2003 |
| JP | 2007-63284 | 3/2007 |
| JP | 2010-59080 | 3/2010 |
| JP | 2010-059081 | 3/2010 |
| JP | 2011-147392 B1 | 10/2011 |
| JP | 2013-079204 | 5/2013 |
| WO | WO 2010/001824 A1 | 7/2010 |

OTHER PUBLICATIONS

Sato et al., "Antimalarial activity of 6-(1,2,6,7-tetraoxaspiro[7.11]nonadec-4-yl)hexan-1-ol (N-251) and its carboxylic acid derivatives," Parasitology International, 60:488-492, 2011.
Ueda et al., "New Preclinical Antimalarial Drugs Potently Inhibit Hepatitis C Virus Genotype 1b RNA Replication," PLOS ONE, 8(8):1-11, 2013.
Paeshuyse et al., "Hemin potentiates the anti-hepatitis C virus activity of the antimalarial drug artemisinin," BBRC, 348:139-144, 2006.
Sato et al., "Antimalarial activity of endoperoxide compound 6-(1,2,6,7-tetraoxaspiro [7.11]nonadec-4-yl) hexan-1-ol," Parasitology International, 60: 270-273, 2011.
Ueda Y et al., BBRC, 409;663-668, 2011.
Kim H-S et al., J. Med. Chem., 44:2357-2361, 2001.
Communication from European Patent Office, Nov. 24, 2015.

* cited by examiner

*Primary Examiner* — Kevin E Weddington
(74) *Attorney, Agent, or Firm* — Joseph H. Kim; JHK Law

(57) ABSTRACT

Provided is a novel anti-HCV agent including as an active ingredient a peroxide derivative represented by the general formula (I). In the general formula (I), C represents an alicyclic hydrocarbon ring group which may be substituted, n represents an integer of from 1 to 6, and R represents a hydrogen atom or a hydroxyalkyl group. The peroxide derivative exhibits potent anti-HCV activity by remarkably suppressing HCV-RNA replication.

15 Claims, 25 Drawing Sheets

ANTI-HCV AGENT

TECHNICAL FIELD

The present invention relates to a novel anti-hepatitis C virus (HCV) agent, and more particularly, to a novel anti-HCV agent, including as an active ingredient a peroxide derivative represented by the general formula (I).

The present application claims priority from Japanese Patent Application No. 2011-219377, which is incorporated herein by reference.

BACKGROUND ART

Approximately 2,000,000 people are infected with hepatitis C virus (HCV) in Japan. It is highly probable that HCV infection causes chronic hepatitis C. Chronic hepatitis C leads to liver cirrhosis and hepatoma, which are lethal diseases, in from 10 to 20 years.

There are several tens of genotypes of HCV. In Japan, ratios of genotype 1b, genotype 2a, and genotype 2b are about 70%, about 20%, and 10%, respectively. At present, therapy with pegylated-interferon (PEG-IFN) in combination with ribavirin (RBV) is standard therapy for chronic hepatitis C (covered by insurance since December 2004). Its curing ratio is 80% or more for genotype 2a or 2b, but is as low as about 55% for genotype 1b. Therapy with telaprevir (HCV protease inhibitor), in addition to the therapy with PEG-IFN in combination with RBV, is scheduled to start, and the triple therapy is expected to increase the curing ratio for genotype 1b as well to about 70 to 80%. However, the following problems have not yet been overcome: a case of discontinued therapy due to exacerbation of a side effect (anemia) of RBV by telaprevir; a case of onset of depression resulting from therapy with IFN; an ineffective case where IFN is not effective; and presence of a large number of older people that cannot be treated with IFN. Accordingly, there is a need for development of a novel anti-HCV agent that can cure the above-mentioned cases as well.

For searching an anti-HCV agent, there is mainly used a reporter assay system (Ikeda M et al., BBRC, 329:1350-1359, 2005) developed based on HCV-replicon-replicating cells (HCV subgenomic RNA autonomously replicates and proliferates in the cells), which were developed by a German group in 1999 (Lohmann V et al. Science, 285:110-113, 1999), or cells in which full-length HCV RNA with a structural region of HCV autonomously replicates (full-length HCV-RNA-replicating cells) (Ikeda M et al., J. Virol. 76:2997-3006, 2002). The inventors of the present invention developed an assay system using OR6 cells as another assay system (JP 4009732 B2). In the OR6 cells, HCV RNA is linked to RNA encoding renilla luciferase gene. Therefore, the assay system allows a level of HCV-RNA replication to be quantitatively monitored by simply measuring renilla luciferase activity, and has been markedly improved in terms of time and cost as compared to conventional RNA quantification. In the assay system using OR6 cells, an HCV-RNA replication inhibitor can be searched from a compound library or the like. Therefore, a large number of compounds have already been screened, and a plurality of compounds each exhibiting anti-HCV activity have been selected, some of which have been tested towards clinical application. The inventors of the present invention found a statin agent (Patent Literature 1: JP 2007-63284 A), teprenone and 5-HETE (Patent Literature 2: JP 2010-59080A), oncostatin M (Patent Literature 3: JP2010-59081A), and the like as anti-HCV agents by screening existing drugs and the like through use of the assay system using OR6 cells.

The above-mentioned reporter assay system is an assay system that is useful in that the level of HCV-RNA replication can be simply and quantitatively monitored. Hitherto, however, there has been a problem in that such assay system can be utilized only for cells derived from a human hepatoma-derived cell line, HuH-7 (Nakabayashi H et al., Cancer Res. 42:3858-3863, 1982). A clinical trial of a compound obtained by screening using only the HuH-7-derived assay system as an anti-HCV agent candidate involves a risk in terms of a therapeutic effect. Further, screening using cells of only one kind may miss a drug exhibiting anti-HCV activity. In order to reduce such risk, the inventors of the present invention worked on development of cells that were derived from a human culture cell line different from HuH-7 and were able to be used for an assay system, and in 2008, succeeded in developing cells (ORL8 and ORL11) derived from a human hepatoma cell line, Li23, in which the level of HCV-RNA replication can be monitored by measuring renilla luciferase activity (WO 2010/026965 A1, Kato N et al., Virus Res. 146:41-50, 2009). After that, anti-HCV agent candidates reported previously were evaluated by assay systems using OR6 cells and ORL8 cells. As a result, in about half of the cases, a 50% effective concentration ($EC_{50}$) value was high 3-fold or more, or was as low as one-third or less as compared to values reported previously. In addition, also in comparison between the assay systems using OR6 cells and ORL8 cells, a drug (methotrexate) having different $EC_{50}$ values up to 2,000-fold was found (Non Patent Literature 1: Ueda Y et al., BBRC, 409:663-668, 2011).

According to a previous report on artemisinin, a drug used as an antimalarial agent, an assay system using HuH-7-derived HCV-replicon-replicating cells demonstrates that artemisinin has anti-HCV activity, though the activity is weak (Non Patent Literature 2: Paeshuyse J et al., BBRC, 348:139-144, 2006). The inventors of the present invention performed assays using full-length HCV-RNA-replicating cells (e.g., OR6 cells and ORL8 cells) derived from the above-mentioned two kinds of cell lines (HuH-7 and Li23). However, artemisinin had an $EC_{50}$ in the OR6 cells of 81 µM and an $EC_{50}$ in the ORL8 cells of 23 µM, which were high concentrations, revealing that artemisinin was not a potential anti-HCV agent candidate (Non Patent Literature 1: Ueda Y et al., BBRC, 409:663-668, 2011). As another antimalarial agent, the inventors of the present invention reported a compound N-89 obtained by screening using antimalarial activity as an indicator (Patent Literature 4: JP 2000-229965 A, Non Patent Literature 3: Kim H-S et al., J. Med. Chem., 44:2357-2361, 2001). In addition, there is also a report that a compound N-251 has antimalarial activity (Patent Literature 5: JP 4289911 B2 and Non Patent Literature 4: Sato A et al., Parasitology Int., 60:270-273, 2011). However, those compounds have structures quite different from that of artemisinin.

There is a demand for development of a highly safe anti-HCV agent that exhibits potent anti-HCV activity without being influenced by genetic diversity of the virus.

CITATION LIST

Patent Literature

[PTL 1] JP 2007-63284 A
[PTL 2] JP 2010-59080 A
[PTL 3] JP 2010-59081 A
[PTL 4] JP 2000-229965 A
[PTL 5] JP 4289911 B2

Non Patent Literature

[NPL 1] Ueda Y et al., BBRC, 409:663-668, 2011
[NPL 2] Paeshuyse J et al., BBRC, 348:139-144, 2006
[NPL 3] Kim H-S et al., J. Med. Chem., 44:2357-2361, 2001
[NPL 4] Sato A et al., Parasitology Int., 60:270-273, 2011

SUMMARY OF INVENTION

Technical Problem

An object of the present invention is to provide a novel anti-HCV agent that exhibits potent anti-HCV activity without being influenced by the genetic diversity of a virus.

Solution to Problem

The inventors of the present invention have made intensive studies in order to achieve the object. As a result, the inventors have found that a peroxide derivative can potently suppress HCV-RNA replication at a low concentration of 1 μM or less. Thus, the present invention has been completed.

That is, the present invention includes the following.

1. A novel anti-HCV agent, including as an active ingredient a peroxide derivative represented by the general formula (I):

Formula (I)

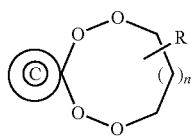

where C represents an alicyclic hydrocarbon ring group which may be substituted, n represents an integer of from 1 to 6, and R represents a hydrogen atom or a hydroxyalkyl group.

2. A novel anti-HCV agent according to Item 1, in which the peroxide derivative includes a peroxide derivative represented by the general formula (I), where C represents an alicyclic hydrocarbon ring group which may have a lower alkyl group as a substituent.

3. A novel anti-HCV agent according to Item 1, in which the peroxide derivative includes a peroxide derivative represented by the general formula (I), where C represents an alicyclic hydrocarbon ring group free of a substituent.

4. A novel anti-HCV agent according to Item 1, in which the peroxide derivative includes a peroxide derivative represented by the general formula (I), where C represents a cyclododecylidene group free of a substituent.

5. A novel anti-HCV agent according to any one of Items 1 to 4, in which the peroxide derivative includes a peroxide derivative represented by the general formula (I), where n represents from 1 to 4.

6. A novel anti-HCV agent according to any one of Items 1 to 5, in which the peroxide derivative includes a compound represented by the following formula (II) or formula (III).

Formula (II)

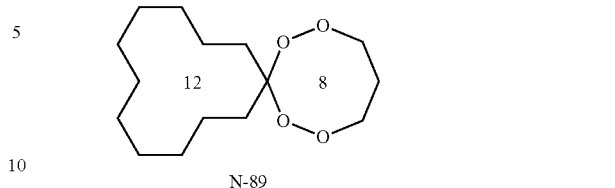

N-89

Formula (III)

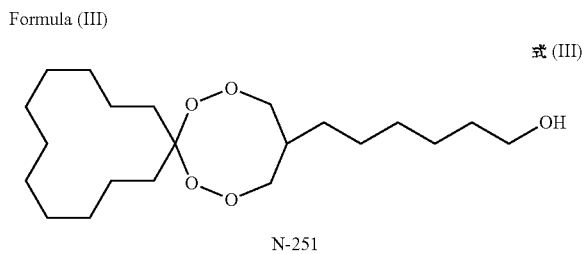

N-251

7. A novel anti-HCV agent according to any one of Items 1 to 6, in which the peroxide derivative has an inhibitory action on HCV-RNA replication.

8. A novel HCV agent according to any one of Items 1 to 7, in which the novel HCV agent is used in combination with at least one drug selected from the group consisting of interferon (IFN), ribavirin (RBV), cyclosporine (CsA), and fluvastatin (FLV).

9. A therapeutic and/or prophylactic composition for hepatitis C, including the novel anti-HCV agent according to any one of Items 1 to 7.

10. A therapeutic and/or prophylactic composition for hepatitis C according to Item 9, further including at least one drug selected from the group consisting of IFN, RBV, CsA, and FLV.

11. A therapeutic and/or prophylactic kit for hepatitis C, including the novel anti-HCV agent according to any one of Items 1 to 7.

12. A therapeutic and/or prophylactic kit according to Item 11, further including at least one drug selected from the group consisting of IFN, RBV, CsA, and FLV.

13. A therapeutic and/or prophylactic method for hepatitis C, including administering the novel anti-HCV agent according to any one of Items 1 to 7 to a patient.

14. A therapeutic and/or prophylactic method according to Item 13, further including administering at least one drug selected from the group consisting of IFN, RBV, CsA, and FLV to the patient.

15. A therapeutic and/or prophylactic method according to Item 13 or 14, in which the administering of the novel anti-HCV agent to the patient and the administering of the at least one drug selected from the group consisting of IFN, RBV, CsA, and FLV to the patient are carried out at the same or different timings.

16. A method of suppressing or inhibiting at least anyone of HCV infection, replication, particle production, and re-infection, in particular, suppressing or inhibiting HCV replication, the method including using the novel anti-HCV agent according to any one of Items 1 to 7.

Advantageous Effects of Invention

The novel anti-HCV agent of the present invention has been comprehensively assessed using cells derived from a plurality of HCV strains and cell lines, and hence is considered to exhibit a potent anti-HCV action even in HCV strains having genetic diversity and cell lines having different genetic backgrounds. In addition, according to the novel anti-HCV agent of the present invention, HCV-RNA-replicating cells from which HCV-RNA has been completely eliminated, i.e., cured cells were able to be obtained. Accordingly, the use of the novel anti-HCV agent of the present invention can be highly expected to remarkably increase a therapeutic effect on hepatitis C and markedly improve a curing ratio. In addition, the anti-HCV agent of the present invention is considered to have low cytotoxicity and high safety without being influenced by the genetic diversity and mutation of HCV, and hence is very useful. Further, a prominent feature of the anti-HCV agent of the present invention is to exhibit a synergistic effect of anti-HCV activities when used in combination with the existing anti-HCV agent (e.g., RBV, CsA, or FLV). The administration of IFN or RBV exhibits a side effect, and hence it is considered that the anti-HCV agent of the present invention in combination with IFN or RBV can markedly reduce the dosage of IFN or RBV and can remarkably alleviate the side effect.

DESCRIPTION OF EMBODIMENTS

Figure 1:
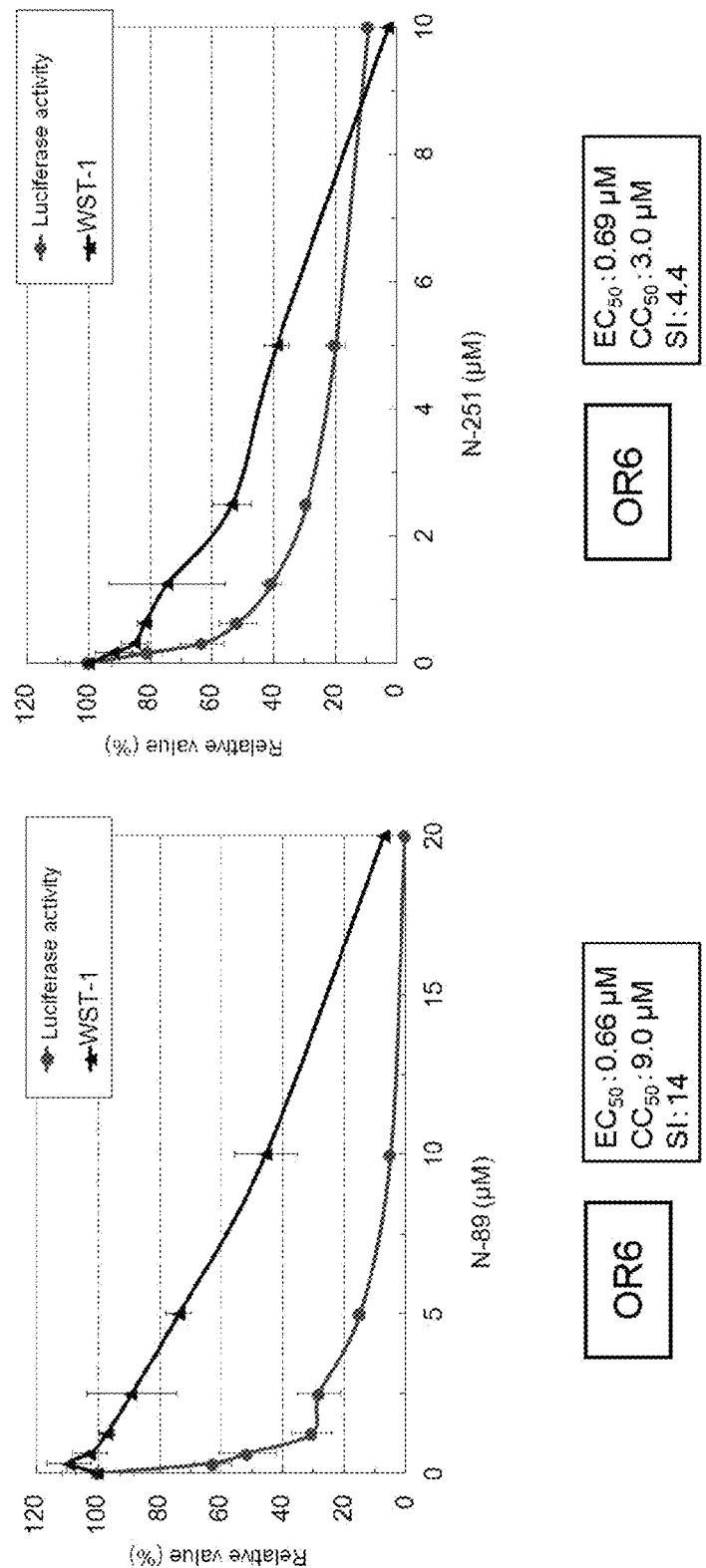
FIG. 1 shows the anti-HCV activities of N-89 and N-251 in OR6 cells (Example 1).

The present invention provides a novel anti-HCV agent. In general, the term "anti-HCV action" means a suppressive or inhibitory action on any one of HCV infection, replication, particle production, and re-infection. In the present invention, the term "anti-HCV" preferably means the suppression or inhibition of HCV replication, in particular, the suppression or inhibition of HCV-RNA replication. It should be noted that the application of the "anti-HCV agent" encompasses in vivo and in vitro ones, and the aspect of use in vivo is described later as a "therapeutic and/or prophylactic composition."

The novel anti-HCV agent of the present invention includes as an active ingredient a peroxide derivative represented by the following formula (I):

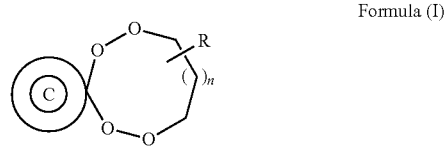

Formula (I)

(where C represents an alicyclic hydrocarbon ring group which may have a substituent, n represents an integer of from 1 to 6, and R represents a hydrogen atom or a hydroxyalkyl group).

In the general formula (I), examples of the alicyclic hydrocarbon ring group which may have a substituent represented by C include: monocyclic alicyclic hydrocarbon groups having 3 to 12 carbon atoms such as cyclopropylidene, cyclobutylidene, cyclopentylidene, cyclohexylidene, cycloheptylidene, cyclooctylidene, cyclononylidene, cyclodecylidene, cycloundecylidene, and cyclododecylidene groups; and bridged ring or polycyclic alicyclic hydrocarbon groups such as bicyclobutylidene, bicyclooctylidene, bicyclononylidene, norbornylidene, norborenylidene, adamantylidene, and noradamantylidene groups. Of those, monocyclic alicyclic hydrocarbon groups having 6 to 12 carbon atoms or an adamantylidene group is preferred, and a cyclohexylidene, cyclododecylidene, or adamantylidene group is more preferred. Further, examples of the substituent which may be possessed by the alicyclic hydrocarbon ring group represented by C include: linear or branched lower alkyl groups having 1 to 6 carbon atoms, including linear or various branched pentyl groups, such as methyl, ethyl, n-propyl, i-propyl, n-butyl, i-butyl, sec-butyl, and tert-butyl groups; and linear or branched lower alkoxy groups having 1 to 6 carbon atoms, including linear or various branched pentyloxy groups, such as methoxy, ethoxy, n-propoxy, i-propoxy, n-butoxy, i-butoxy, sec-butoxy, and tert-butoxy groups. Of those, lower alkyl groups are preferred and a tert-butyl group is more preferred. Of the compounds of the present invention, a preferred compound is a compound represented by the general formula (1), where C represents an alicyclic hydrocarbon ring group which may have a lower alkyl group as a substituent or a compound represented by the general formula (1), where C represents an alicyclic hydrocarbon ring group free of a substituent. A more preferred compound is a compound represented by the general formula (1), where C represents a 4-tert-butylcyclohexylidene, cyclododecylidene, or adamantylidene group, and a still more preferred compound is a compound represented by the general formula (1), where C represents a cyclododecylidene group and n represents from 1 to 4.

In addition, R in the general formula (I) represents a hydrogen atom or a hydroxyalkyl group. A hydroxyalkyl group in which a hydroxy group is bonded to a terminal of its alkyl chain is preferred as the hydroxyalkyl group. In addition, a linear hydroxyalkyl group in which its alkyl chain (alkylene group) has 1 to 10 (preferably 1 to 6) carbon atoms is preferred. Examples thereof include alkylene groups having 1 to 10 carbon atoms such as a methylene group, an ethylene group, a propylene group, an n-butylene group, an n-pentylene group, an n-hexylene group, an n-heptylene group, an n-octylene group, an n-nonylene group, and an n-decylene group.

When R in the general formula (I) represents a hydroxyalkyl group, the hydroxyalkyl group is preferably bonded at the α-position or β-position with respect to a peroxy group in an oxo ring, i.e., the 6-position or 7-position of a 1,2,4,5-tetroxane ring. A compound represented by the general formula (I) in which the hydroxyalkyl group is bonded at that position has improved solubility in a solvent even when the number of members of the oxo ring is large.

The peroxide derivative represented by the general formula (I) may be synthesized according to the following scheme. Specifically, the peroxide derivative may be manufactured by a method disclosed in JP 2000-229965 A or JP 4289911 B2.

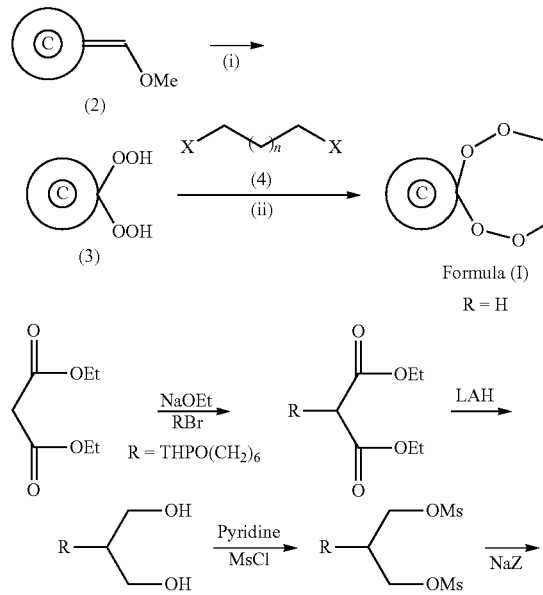

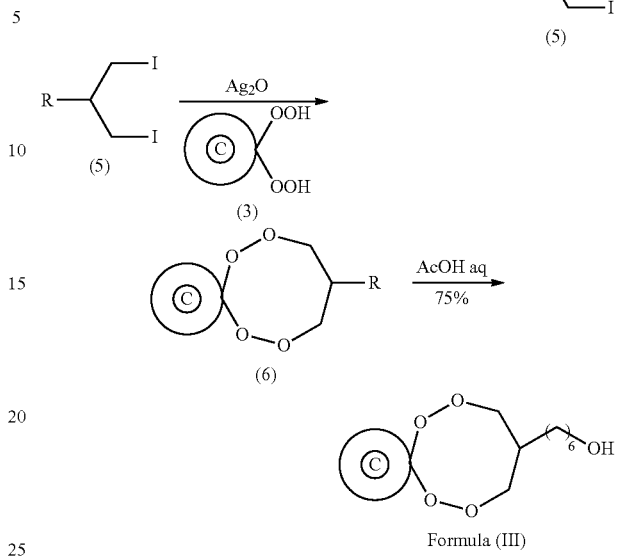

The peroxide derivative contained in the novel HCV agent of the present invention is specifically exemplified by compounds shown below. The peroxide derivative contained in the novel HCV agent of the present invention is most preferably a compound represented by the following formula (II) (1,2,6,7-tetraoxaspiro[7,11]nonadecane) (herein sometimes referred to as "N-89") or a compound represented by the formula (III) (6-(1,2,6,7-tetraoxaspiro[7,11]nonadec-4-yl) (herein sometimes referred to as "N-251).

Formula (II)

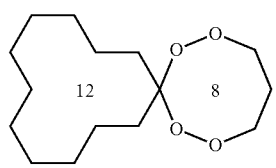

Formula (III)

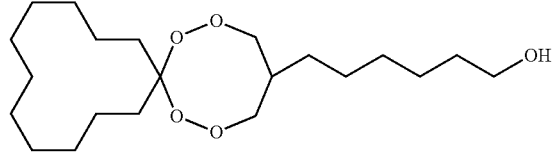

The present invention provides a therapeutic and/or prophylactic composition for the treatment and/or prophylaxis of hepatitis C, the composition containing the novel anti-HCV agent. Hepatitis C may be classified into acute hepatitis C and chronic hepatitis C, and the therapeutic and/or prophylactic composition according to the present invention is suited for chronic hepatitis C.

The compound according to the general formula (I) exhibits a potent anti-HCV action alone, and hence a composition containing as an active ingredient the anti-HCV agent of the present invention alone may be used as the therapeutic and/or prophylactic composition for the treatment of hepatitis C according to the present invention. In addition, the therapeutic and/or prophylactic composition of the present invention may be used in combination with interferon (IFN), ribavirin (RBV), cyclosporine (CsA), fluvastatin (FLV), telaprevir, and/or pitavastatin (PTV). In addition, the therapeutic and/or prophylactic composition of the present invention may further contain as an active ingredient IFN or the like described above. The anti-HCV agent according to the present invention synergistically enhances the anti-HCV activities of IFN, RBV, CsA, and FLV, in particular. IFN is preferably IFN-α or IFN-β, particularly preferably IFN-α. In addition, IFN may have been subjected to modification such as pegylation (PEG-IFN).

The therapeutic and/or prophylactic composition according to the present invention may be administered to a subject to be tested through any one of oral, parenteral, or local routes, and is preferably orally administered. Further, the therapeutic and/or prophylactic composition may be formulated into oral formulations such as powders, tablets, fine granules, pills, capsules, and granules, and parenteral formulations such as ophthalmic solutions, injections, and suppositories, which are generally manufactured using pharmaceutically acceptable carrier, excipient, and other additives. Examples of the pharmaceutically acceptable carrier, excipient, and other additives include glucose, lactose, gelatin, mannitol, starch paste, magnesium trisilicate, corn starch, keratin, and colloidal silica. Additional examples thereof include aids such as a stabilizer, a bulking agent, a colorant, and a fragrance. Each of those formulations may be manufactured by a known conventional manufacturing method by a person skilled in the art. The blending amount of the peroxide compound as the active ingredient contained in the therapeutic and/or prophylactic composition of the present invention is preferably from 0.1 to 100% by weight, more preferably from 0.1 to 80% by weight, suitably from 0.1 to 50% by weight. Further, a dosage per day cannot be generally determined because the dosage varies depending on, for example, the symptom, body weight, age, and gender of a patient, but the therapeutic and/or prophylactic composition is preferably administered at a dosage of generally from 0.1 to 1,000 mg, preferably from 1 to 600 mg per day for an adult human in one portion or about two to four divided portions.

The present invention also encompasses a therapeutic and/or prophylactic kit for hepatitis C, in which the above-mentioned therapeutic and/or prophylactic composition is provided in the aspect of a kit. Herein, the term "kit" means a package including a container (e.g., a bottle, a plate, a tube, or a dish) that holds certain materials, preferably including instructions for use of these materials. The instructions may be written or printed on paper or any other medium, or may be recorded on an electronic medium such as a magnetic tape, a computer-readable disk or tape, or a CD-ROM.

The kit according to the present invention has only to include the novel anti-HCV agent according to the present invention, and may include the therapeutic and/or prophylactic composition according to the present invention. The kit according to the present invention may include a composition including an ingredient different from that of the novel anti-HCV agent. The composition including an ingredient different from that of the novel anti-HCV agent according to the present invention is not particularly limited and is exemplified by a therapeutic composition for hepatitis C, including as an active ingredient IFN, CsA, FLV, telaprevir, and/or PTV.

When the kit includes two or more kinds of compositions, the kit may include the compositions in separate containers (e.g., divided bottles), or may include the compositions in a non-divided single container. In addition, the kit may include a container that holds a diluent, a solvent, a washing liquid, or any other reagent. Further, in addition to the foregoing, the kit may include an instrument required for its application to a therapeutic and/or prophylactic method for hepatitis C.

The form of the kit is particularly advantageous, for example, when separate ingredients are preferably administered in different dosage forms (e.g., oral and parenteral) or administered at different dosages, or a prescribing physician is to titrate each of the ingredients according to the combination. A use method for the kit according to the present invention has only to conform to the above-mentioned use form of the composition or the like.

In addition, the therapeutic and/or prophylactic method according to the present invention may be an aspect in which the above-mentioned novel anti-HCV agent, therapeutic and/or prophylactic composition, or therapeutic and/or prophylactic kit is applied. That is, the therapeutic method according to the present invention has only to include the step of administering the novel anti-HCV agent according to the present invention to a patient, and may further include the step of administering IFN, CsA, FLV, and/or PTV. The application of the novel anti-HCV agent or the like in the therapeutic and/or prophylactic method according to the present invention has only to conform to the above-mentioned use form.

EXAMPLES

Hereinafter, the novel anti-HCV agent of the present invention is described by way of Examples. However, it should be appreciated that the present invention is by no means limited to the description of Examples.

Reference Example 1

Cells and Evaluation Methods for Anti-HCV Activity and Cytotoxic Effect Used in the Present Invention Assay systems using OR6 cells (HCV-O strain), 1B-4R cells (HCV-1B-4 strain), and AH1R cells (HCV-AH1R strain) as HuH-7 cell-derived full-length HCV-RNA-replicating cells, and ORL8 cells (HCV-O strain), ORL11 cells (HCV-O strain), 1B-4RL cells (HCV-1B-4 strain), and KAH5RL cells (HCV-KAH5 strain) as Li23 cell-derived full-length HCV-RNA-replicating cells were used for the quantitative analysis of anti-HCV activity and evaluation of a cytotoxic effect in the present invention. The three cell lines, i.e., the 1B-4R cells, the 1B-4RL cells, and the KAH5RL cells have been disclosed in WO 2010/026965 A1. The AH1R cells may be produced with reference to Mori K et al., BBRC, 371:104-109, 2008 and WO 2010/026965 A1. In addition, all the HCV strains belong to genotype 1b.

For the anti-HCV activity, renilla luciferase activity was quantitatively measured and a 50% effective concentration ($EC_{50}$) was calculated. As necessary, an increase or decrease in expression level of an HCV protein (core protein) was examined by a Western blot method.

For the cytotoxic effect, measurement was performed according to the protocol of a commercially available WST-1 cell proliferation assay system (Premix WST-1 Cell Proliferation Assay System: Takara Bio Inc.) and a 50% cytotoxic concentration ($CC_{50}$) was calculated.

In the measurement of the renilla luciferase activity and the measurement by the WST-1 method, experiments were performed in three wells independent of each other, and their means and standard deviation were calculated.

A selective cytotoxicity value (selective index: SI) was calculated by dividing the $CC_{50}$ value by the $EC_{50}$ value.

Example 1

Anti-HCV Activities of N-89 and N-251 in OR6 Cells

The anti-HCV activities of N-89 and N-251 were examined using OR6 cells and the $EC_{50}$ values were calculated.

OR6 cells, which had been cultured in general medium for subculture, were plated onto a 24-well plate ($2\times10^4$ cells in 1 mL of medium for Li23 cell line per well) and cultured. After 24 hours, N-89 was added so as to achieve concentrations of 20 µM, a 2-fold dilution series from 20 µM (10, 5, 2.5, 1.3, 0.63, and 0.31 µM), and 0, or N-251 was added so as to achieve concentrations of 10 µM, a 2-fold dilution series from 10 µM (5, 2.5, 1.3, 0.63, 0.31, and 0.16 µM), and 0. The renilla luciferase activities were measured 72 hours after the culture. N-89 and N-251 were diluted with DMSO.

As a result of the measurement, the $EC_{50}$ values of N-89 and N-251 were calculated to be 0.66 µM and 0.69 µM, respectively (FIG. 1).

The cytotoxic effects of N-89 and N-251 were examined using OR6 cells and the $CC_{50}$ values were calculated.

OR6 cells, which had been cultured in general medium for subculture, were plated onto a 96-well plate ($1\times10^3$ cells in 0.1 mL of medium for Li23 cell line per well) and cultured. After 24 hours, N-89 was added so as to achieve concentrations of 20 µM, a 2-fold dilution series from 20 µM (10, 5, 2.5, 1.3, 0.63, and 0.31 µM), and 0, or N-251 was added so as to achieve concentrations of 10 µM, a 2-fold dilution series from 10 µM (5, 2.5, 1.3, 0.63, 0.31, and 0.16 µM), and 0. The WST-1 cell proliferation assay was performed 72 hours after the culture, and the $CC_{50}$ values were calculated.

As a result of the measurement, the $CC_{50}$ values of N-89 and N-251 were calculated to be 9.0 µM and 3.0 µM, respectively (FIG. 1).

Taken together, the results showed that the SI value of N-89 was 14 and the SI value of N-251 was 4.4.

Example 2

Analysis of Influences of N-89 and N-251 on HCV Core Protein Expression in OR6 Cells The Western blot analysis of an HCV core protein was performed in order to confirm the anti-HCV activities of N-89 and N-251 in OR6 cells.

OR6 cells, which had been cultured in general medium for subculture, were plated onto a 6-well plate ($5\times10^4$ cells in 3 mL of medium for Li23 cell line per well) and cultured. After 24 hours, N-89 was added so as to achieve concentrations of 20 µM, a 2-fold dilution series from 20 µM (10, 5, 2.5, 1.3, 0.63, and 0.31 µM), and 0, and N-251 was added so as to achieve concentrations of 10 µM, a 2-fold dilution series from 10 µM (5, 2.5, 1.3, 0.63, 0.31, and 0.16 µM), and 0. N-89 and N-251 were diluted with DMSO. After 72 hours, sampling was performed with 100 µL of 2×SDS buffer. 10 µL of a sample were applied to SDS-PAGE electrophoresis and subjected to Western blot analysis using an anti-HCV core antibody and an anti-β-actin antibody according to a conventional method. For the detection of β-actin, a sample diluted 10-fold with 2×SDS buffer in advance was used because the expression amount of β-actin was high.

Figure 2:
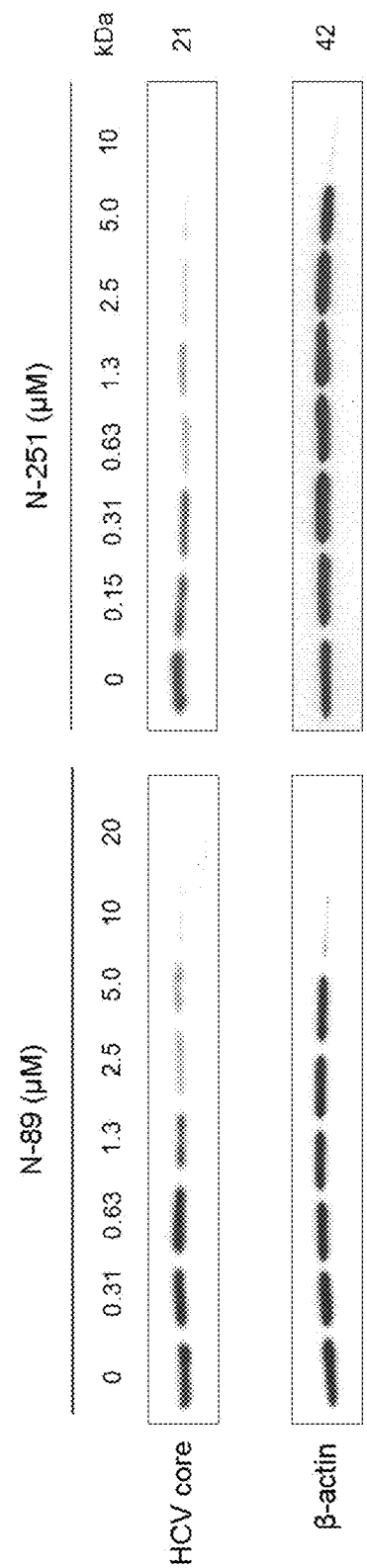
FIG. 2 shows the results of analysis of the influences of N-89 and N-251 on HCV core protein expression in OR6 cells (Example 2).

The analysis confirmed that the level of the HCV core protein reduced depending on the concentrations of N-89 and N-251 (FIG. 2). Reductions in amount of the core protein were observed at around the $EC_{50}$ values (0.66 and 0.69 µM) of N-89 and N-251, which had been obtained in the reporter assay, whereas no reduction in level of β-actin was observed at these concentrations. Thus, the results were considered to reflect the anti-HCV activities. However, remarkable reductions in β-actin were found in concentration regions of 10 µM or more of N-89 and N-251, and hence the anti-HCV activities were considered to be due to cytotoxic effects.

Example 3

Anti-HCV Activities of N-89 and N-251 in ORL8 Cells

The anti-HCV activities of N-89 and N-251 were examined using ORL8 cells and the $EC_{50}$ values were calculated. An experimental scale and schedule are the same as those in Example 1.

N-89 and N-251 were added so as to achieve concentrations of 5 µM, a 2-fold dilution series from 5 µM (2.5, 1.3, 0.63, 0.31, 0.16, and 0.08 µM), and 0. The luciferase activities were measured 72 hours after the culture.

Figure 3:
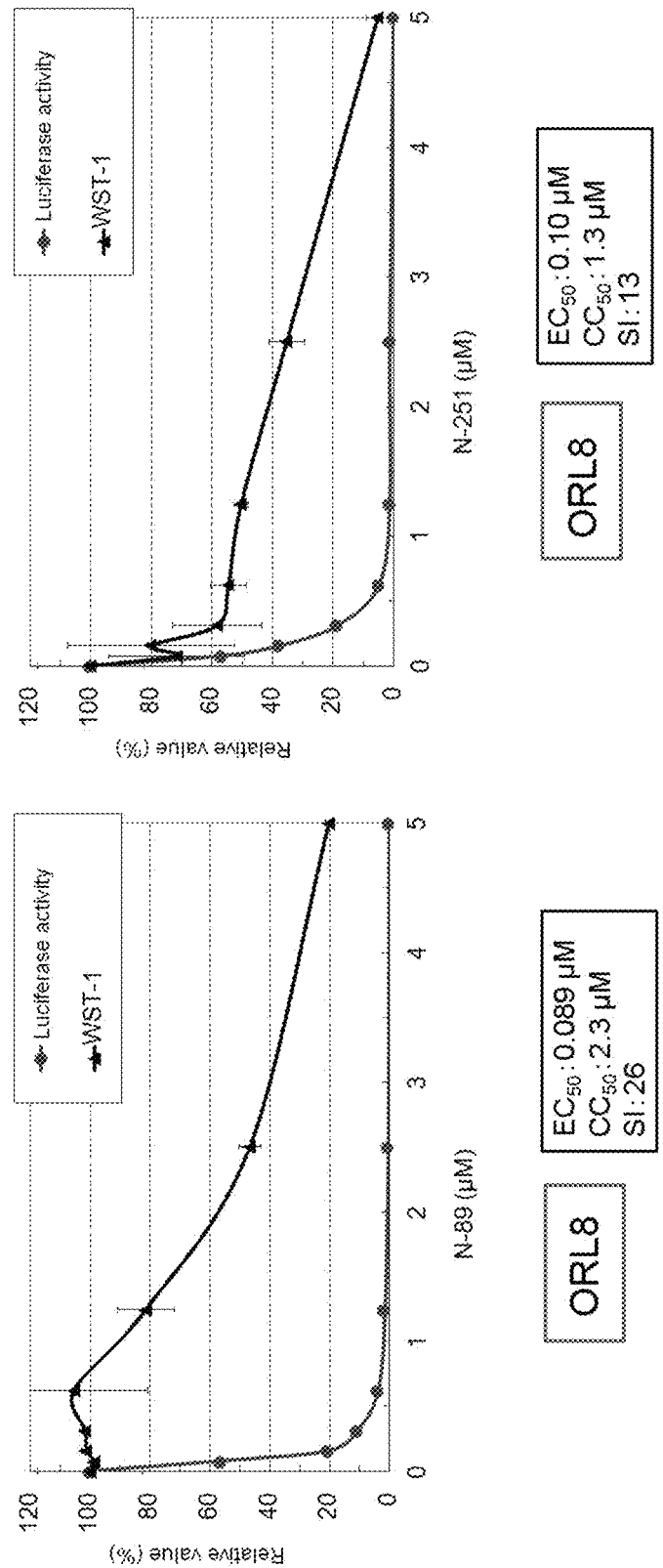
FIG. 3 shows the anti-HCV activities of N-89 and N-251 in ORL8 cells (Example 3).

As a result of the measurement, the $EC_{50}$ values of N-89 and N-251 were calculated to be 0.089 µM and 0.10 µM, respectively (FIG. 3).

The cytotoxic effects of N-89 and N-251 were examined using ORL8 cells and the $CC_{50}$ values were calculated. An experimental scale and schedule are the same as those in Example 1.

N-89 and N-251 were added so as to achieve concentrations of 5 µM, a 2-fold dilution series from 5 µM (2.5, 1.3, 0.63, 0.31, 0.16, and 0.08 µM), and 0. The WST-1 cell proliferation assay was performed 72 hours after the culture.

As a result of the measurement, the $CC_{50}$ values of N-89 and N-251 were calculated to be 2.3 µM and 1.3 µM, respectively (FIG. 3).

Taken together, the results showed that the SI value of N-89 was 26 and the SI value of N-251 was 13.

Example 4

Analysis of Influences of N-89 and N-251 on HCV Core Protein Expression in ORL8 Cells The Western blot analysis of an HCV core protein was performed in order to confirm the anti-HCV activities of N-89 and N-251 in ORL8 cells.

ORL8 cells, which had been cultured in general medium for subculture, were plated onto a 6-well plate ($5\times10^4$ cells in 3 mL of medium for Li23 cell line per well) and cultured. After 24 hours, N-89 and N-251 were added so as to achieve concentrations of 5 µM, a 2-fold dilution series from 5 µM (2.5, 1.3, 0.63, 0.31, 0.16, and 0.078 µM), and 0. N-89 and N-251 were diluted with DMSO. Sampling was performed with 100 µL of 2×SDS buffer 72 hours after the culture. 10 µL of a sample were applied to SDS-PAGE electrophoresis and subjected to Western blot analysis using an anti-HCV core antibody and an anti-β-actin antibody according to a conventional method. It should be noted that for the detection of β-actin, a sample diluted 10-fold with 2×SDS buffer in advance was used.

Figure 4:
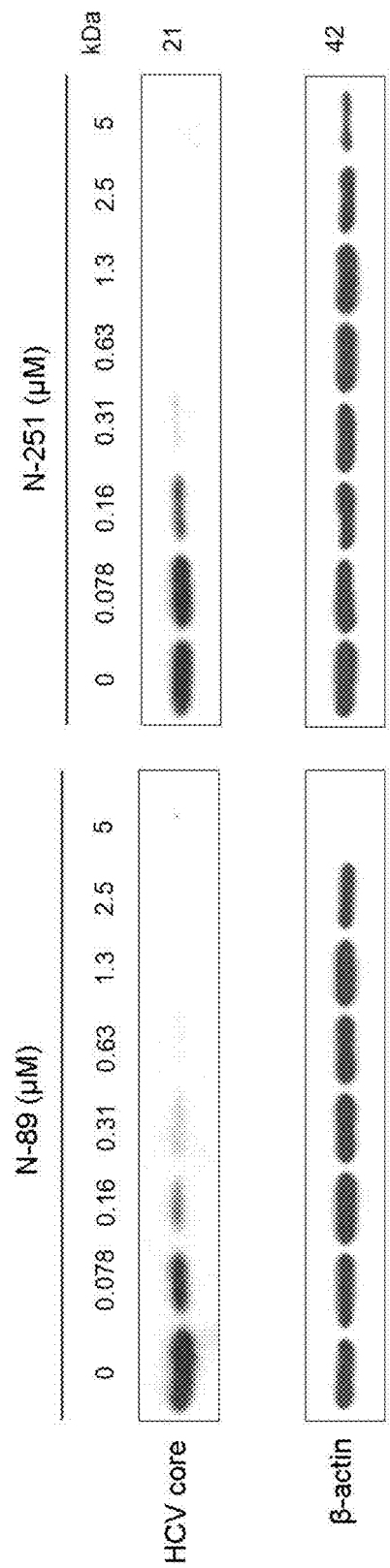
FIG. 4 shows the results of analysis of the influences of N-89 and N-251 on HCV core protein expression in ORL8 cells (Example 4).

The analysis confirmed that the level of the HCV core protein reduced depending on the concentrations of N-89 and N-251 (FIG. 4). Reductions in amount of the core protein were observed at around the $EC_{50}$ values (0.089 and 0.10 µM) of N-89 and N-251, which had been obtained in the reporter assay, whereas no reduction in amount of β-actin was observed at these concentrations. Thus, the results were considered to reflect the anti-HCV activities. However, remarkable reductions in β-actin were found in concentration regions of 5 μM or more of N-89 and N-251, and hence the anti-HCV activities were considered to be due to cytotoxic effects.

Example 5

Anti-HCV Activities of N-89 and N-251 in ORL11 Cells

The anti-HCV activities of N-89 and N-251 were examined using ORL11 cells and the $EC_{50}$ values were calculated. An experimental scale and schedule are the same as those in Example 1.

N-89 was added so as to achieve concentrations of 500 nM, a 2-fold dilution series from 500 nM (250, 125, 63, 31, 16, and 8 nM), and 0. The luciferase activities were measured 72 hours after the culture.

N-251 was added so as to achieve concentrations of 1 μM, a 2-fold dilution series from 1 μM (500, 250, 125, 63, 31, and 16 nM), and 0. The luciferase activities were measured 72 hours after the culture.

Figure 5:
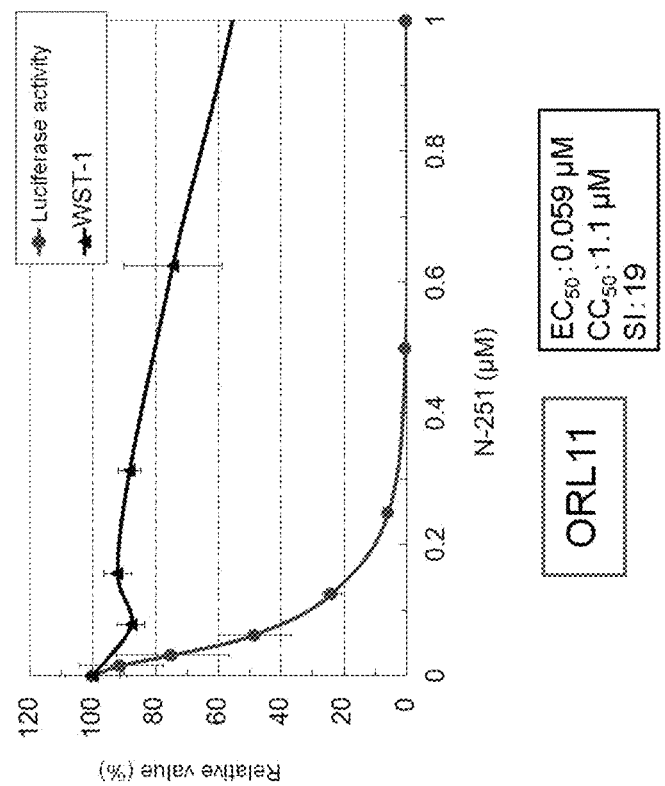
FIG. 5 shows the anti-HCV activities of N-89 and N-251 in ORL11 cells (Example 5).
Figure 5:
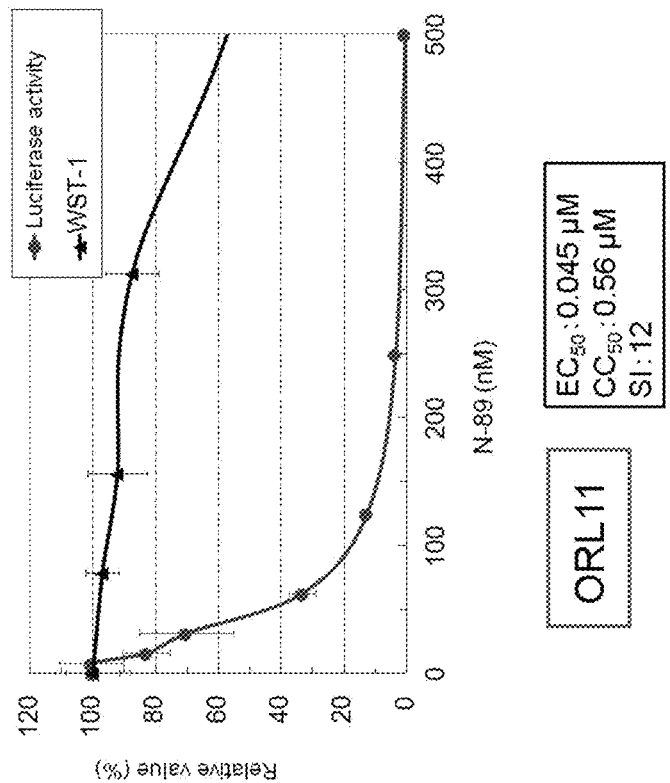

As a result of the measurement, the $EC_{50}$ values of N-89 and N-251 were calculated to be 0.045 μM and 0.059 μM, respectively (FIG. 5).

The cytotoxic effects of N-89 and N-251 were examined using ORL11 cells and the $CC_{50}$ values were calculated. An experimental scale and schedule are the same as those in Example 1.

N-89 was added so as to achieve concentrations of 500 nM, a 2-fold dilution series from 500 nM (250, 125, 63, 31, 16, and 8 nM), and 0, and N-251 was added so as to achieve concentrations of 1 μM, a 2-fold dilution series from 1 μM (500, 250, 125, 63, 31, and 16 nM), and 0. The WST-1 cell proliferation assay was performed 72 hours after the culture. FIG. 5 shows the results of N-89 at concentrations of up to 0.31 μM and N-251 at concentrations of up to 0.63 μM.

As a result of the measurement, the $CC_{50}$ values of N-89 and N-251 were calculated to be 0.56 μM and 1.1 μM, respectively (FIG. 5).

Taken together, the results showed that the SI value of N-89 was 12 and the SI value of N-251 was 19.

Comparative Example 1

Anti-HCV Activity of Artemisinin in OR6 Cells and ORL8 Cells

The anti-HCV activity of artemisinin was examined using OR6 cells and ORL8 cells and the $EC_{50}$ values were calculated. An experimental scale and schedule are the same as those in Example 1.

Artemisinin was added so as to achieve concentrations of 100 μM, a 2-fold dilution series from 100 μM (50, 25, 13, 6.3, 3.1, and 1.6 μM), and 0. The luciferase activities were measured 72 hours after the culture.

Figure 6:
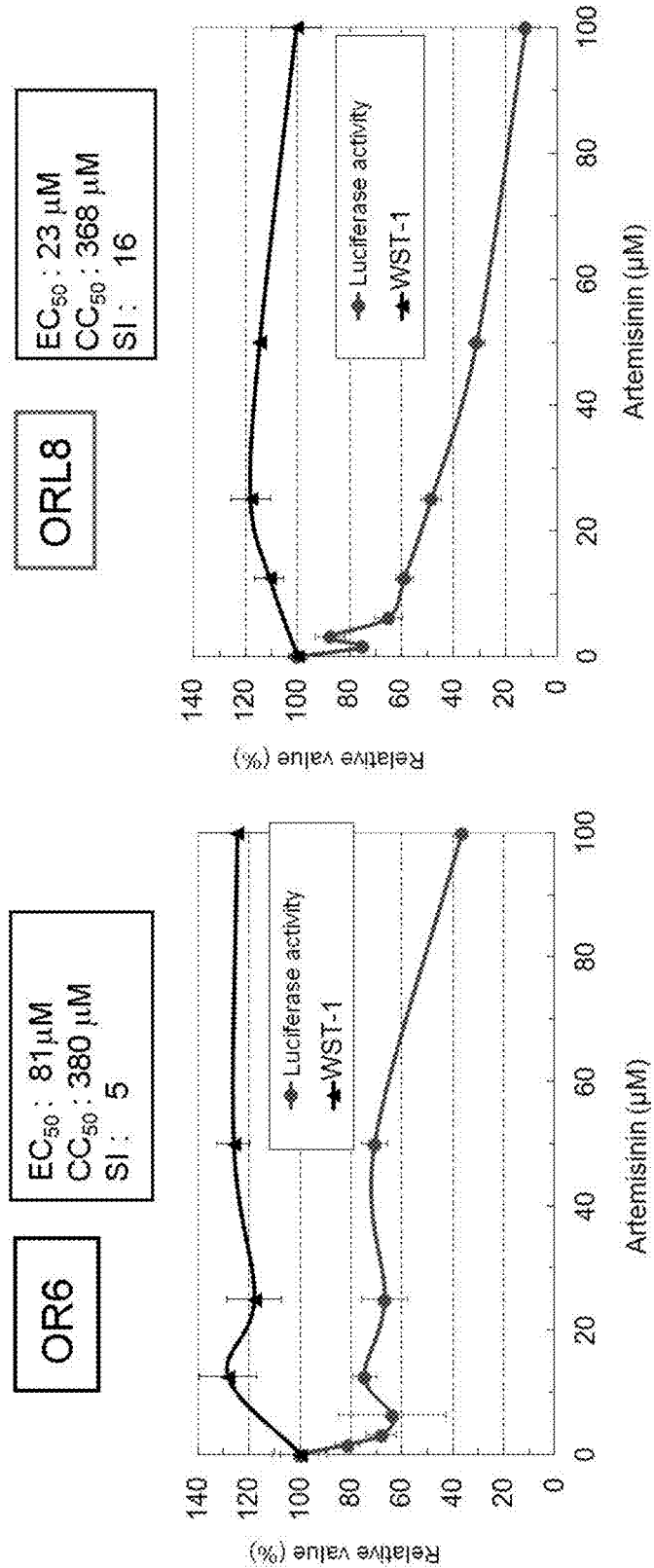
FIG. 6 shows the anti-HCV activities of artemisinin in OR6 cells and ORL8 cells (Comparative Example 1).

As a result of the measurement, the $EC_{50}$ values in OR6 and ORL8 were calculated to be 81 μM and 23 μM, respectively (FIG. 6).

The cytotoxic effect of artemisinin was examined using OR6 and ORL8 cells and the $CC_{50}$ values were calculated. An experimental scale and schedule are the same as those in Example 1. Artemisinin was added so as to achieve concentrations of 400 μM, a 2-fold dilution series from 400 μM (200, 100, 50, 25, and 13 μM), and 0. The WST-1 cell proliferation assay was performed 72 hours after the culture. FIG. 6 shows the results at concentrations of up to 100 μM.

As a result of the measurement, the $CC_{50}$ values in the OR6 cells and the ORL8 cells were calculated to be 380 μM and 368 μM, respectively (FIG. 6).

Taken together, the results showed that the SI value in OR6 was 5 and the SI value in ORL8 was 16. Artemisinin had SI values of 5 and 16 owing to its markedly high $CC_{50}$ values, but had $EC_{50}$ values about 20- to 120-fold higher than those of N-89 and N-251. Thus, artemisinin was judged to have very weak anti-HCV activity.

Example 6

Confirmation that N-89 and N-251 have No Influence on Renilla Luciferase Activity in ORL8 Cells In the ORL8 cells, the anti-HCV activity is evaluated by measuring the activity of renilla luciferase as a product of an exogenous gene introduced so as to be linked to HCV RNA. Therefore, it is necessary to demonstrate that the obtained anti-HCV activity is not due to the direct inhibition of the renilla luciferase activity.

Thus, N-89 or N-251 was added (5 μL) to a lysate (10 μL) of the ORL8 cells (1×10$^5$ cells, medium for Li23 cell line) so as to achieve final concentrations of 0, 5, 10, and 20 μM, and 50 μL of a substrate were further added thereto. Then, the luciferase activity was measured.

Figure 7:
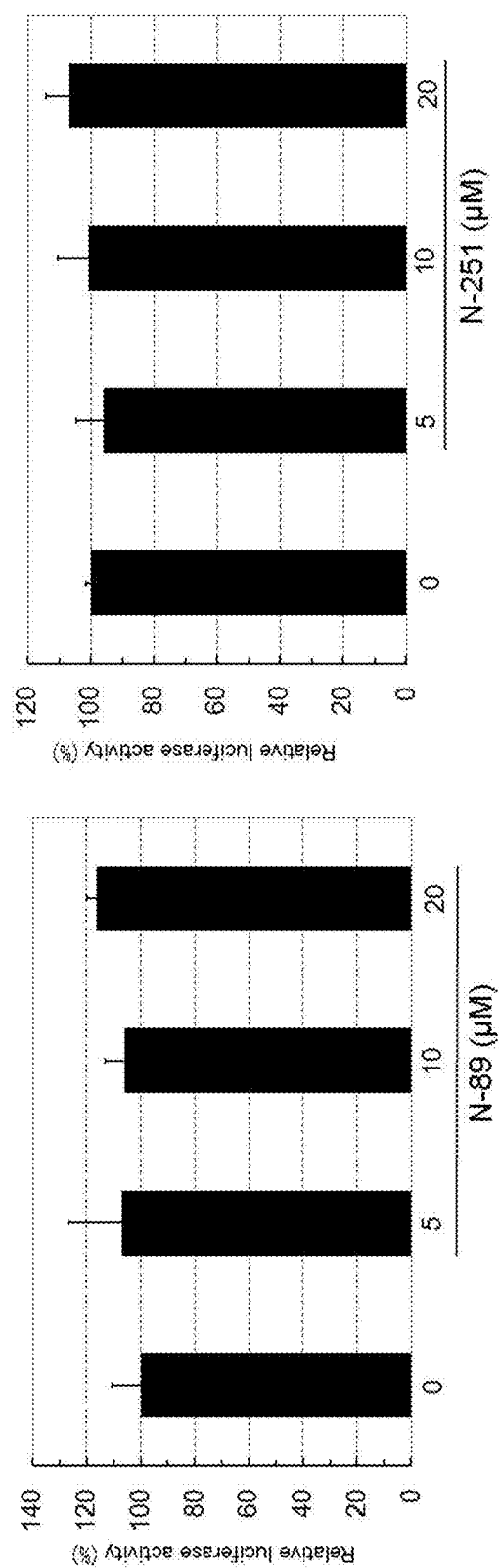
FIG. 7 shows the results of confirmation that N-89 and N-251 have no influence on renilla luciferase activity in ORL8 cells (Example 6).

FIG. 7 shows the results. The numeral "0" shows the results in the case of adding 5 μL of DMSO. An actual luciferase activity value (RL activity value) at 100% on the ordinate axis was $2.2×10^5$ in the case of N-89 and $2.8×10^5$ in the case of N-251.

The results of the measurement revealed that N-89 and N-251 did not show any inhibition on the renilla luciferase activity at concentrations of up to 20 μM.

The results confirmed that the anti-HCV activities of N-89 and N-251 were not due to the inhibition of the renilla luciferase activity.

Example 7

Confirmation that N-89 and N-251 have No Influence on Renilla Luciferase Activity in OR6 Cells Also in OR6 cells (medium for HuH-7 cell line), the renilla luciferase activity was measured by the same technique as in Example 6.

Figure 8:
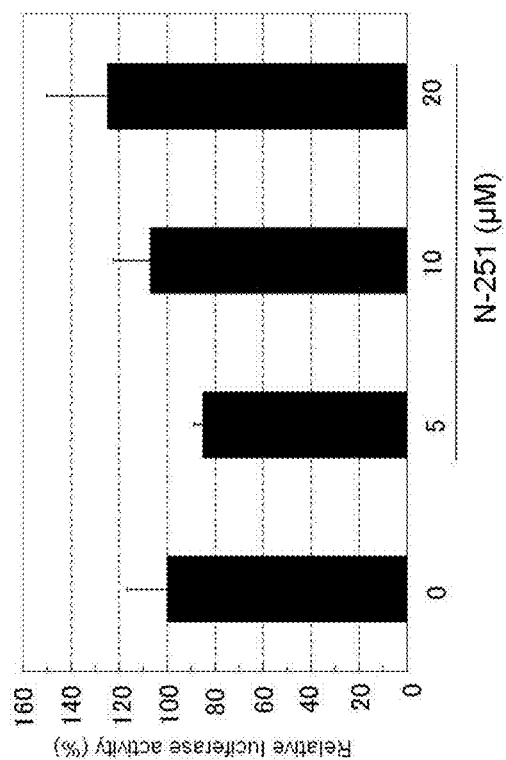
FIG. 8 shows the results of confirmation that N-89 and N-251 have no influence on renilla luciferase activity in OR6 cells (Example 7).
Figure 8:
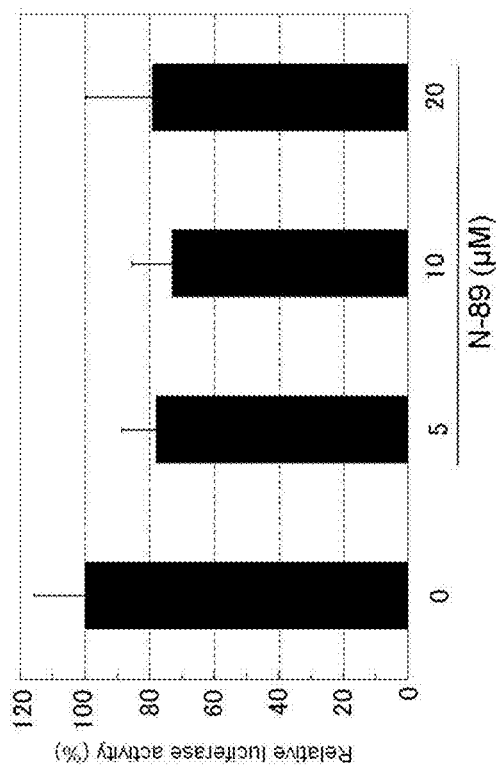

FIG. 8 shows the results. An actual luciferase activity value (RL activity value) at 100% on the ordinate axis was $1.1×10^6$ in both of N-89 and N-251.

It was found that in the case of the OR6 cells, N-89 and N-251 did not show any inhibition on the renilla luciferase activity at concentrations of up to 20 μM as in the ORL8 cells.

The results confirmed that the anti-HCV activities of N-89 and N-251 were not due to the inhibition of the renilla luciferase activity.

Example 8

Anti-HCV Activities of N-89 and N-251 in AH1R Cells

Through the use of cells in which a full-length HCV genome autonomously replicates, derived from the HCV- AH1 strain different from the HCV-O strain (AH1R cells), the anti-HCV activities of N-89 and N-251 were examined and the $EC_{50}$ values were calculated. An experimental scale and schedule are the same as those in Example 1.

N-89 was added so as to achieve concentrations of 500 nM, a 2-fold dilution series from 500 nM (250, 125, 63, 31, 16, and 8 nM), and 0. The luciferase activities were measured 72 hours after the culture.

N-251 was added so as to achieve concentrations of 2 µM, a 2-fold dilution series from 2 µM (1, 0.5, 0.25, 0.13, 0.06, and 0.03 µM), and 0. The luciferase activities were measured 72 hours after the culture.

Figure 9:
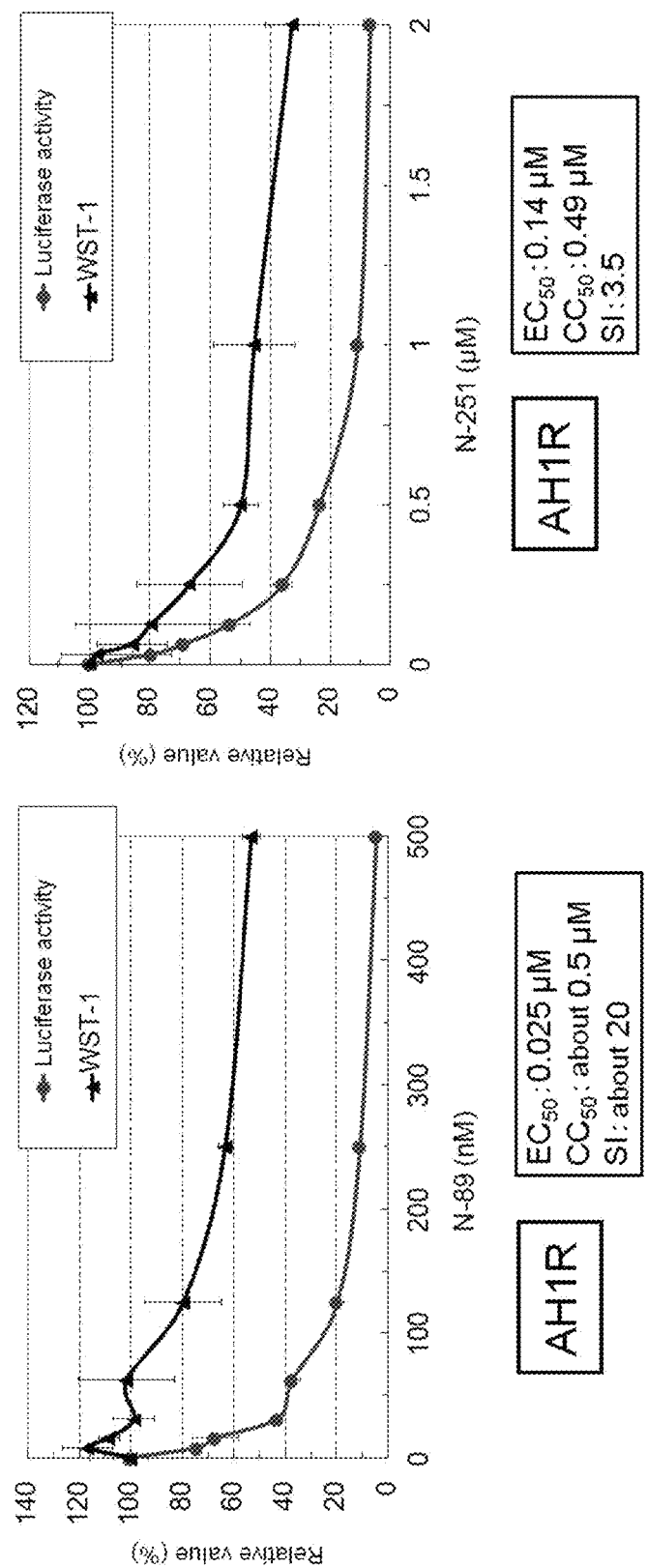
FIG. 9 shows the anti-HCV activities of N-89 and N-251 in AH1R cells (Example 8).

As a result of the measurement, the $EC_{50}$ values of N-89 and N-251 were calculated to be 0.025 µM and 0.14 µM, respectively (FIG. 9).

The cytotoxic effects of N-89 and N-251 were examined using AH1R cells and the $CC_{50}$ values were calculated. An experimental scale and schedule are the same as those in Example 1.

N-89 was added so as to achieve concentrations of 0.5 µM, a 2-fold dilution series from 0.5 µM (0.25, 0.13, 0.06, 0.03, 0.015, and 0.008 µM), and 0, and N-251 was added so as to achieve concentrations of 2 µM, a 2-fold dilution series from 2 µM (1, 0.5, 0.25, 0.13, 0.06, and 0.03 µM), and 0. The WST-1 cell proliferation assay was performed 72 hours after the culture.

As a result of the measurement, the $CC_{50}$ values of N-89 and N-251 were calculated to be about 0.5 µM and 0.49 µM, respectively (FIG. 9).

Taken together, the results showed that the SI value of N-89 was about 20 and the SI value of N-251 was 3.5.

Lower $EC_{50}$ values were obtained in the AH1R cells than in the OR6 cells. However, the $CC_{50}$ values were low, and the SI values of N-89 and N-251 were comparable and low values as compared to OR6, respectively.

Example 9

Anti-HCV Activities of N-89 and N-251 in 1B-4R Cells

Through the use of cells in which a full-length HCV genome autonomously replicates, derived from the HCV-1B-4 strain different from the HCV-O strain (1B-4R cells), the anti-HCV activities of N-89 and N-251 were examined and the $EC_{50}$ values were calculated. An experimental scale and schedule are the same as those in Example 1.

N-89 was added so as to achieve concentrations of 10 µM, a 2-fold dilution series from 10 µM (5, 2.5, 1.3, 0.63, 0.31, and 0.16 µM), and 0. The luciferase activities were measured 72 hours after the culture.

N-251 was added so as to achieve concentrations of 5 µM, a 2-fold dilution series from 5 µM (2.5, 1.3, 0.63, 0.31, 0.16, and 0.08 µM), and 0. The luciferase activities were measured 72 hours after the culture.

Figure 10:
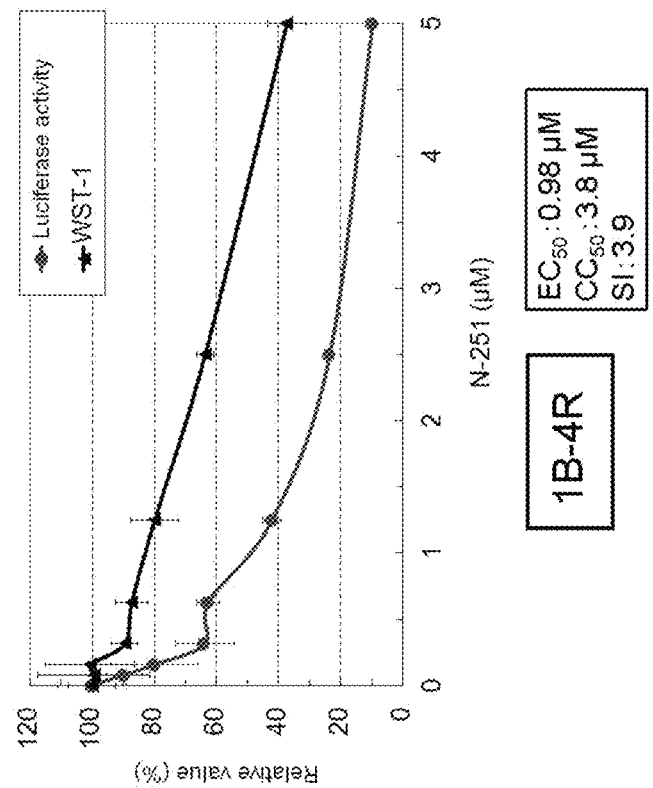
FIG. 10 shows the anti-HCV activities of N-89 and N-251 in 1B-4R cells (Example 9).
Figure 10:
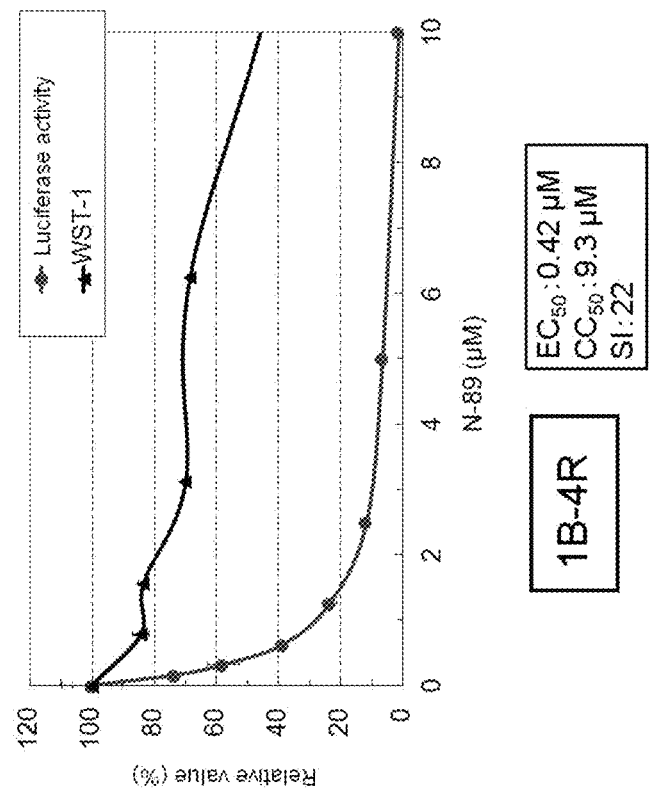

As a result of the measurement, the $EC_{50}$ values of N-89 and N-251 were calculated to be 0.42 µM and 0.98 µM, respectively (FIG. 10).

The cytotoxic effects of N-89 and N-251 were examined using 1B-4R cells and the $CC_{50}$ values were calculated. An experimental scale and schedule are the same as those in Example 1.

N-89 was added so as to achieve concentrations of 50 µM, a 2-fold dilution series from 50 µM (25, 12.5, 6.3, 3.1, 1.6, and 0.8 µM), and 0, and N-251 was added so as to achieve concentrations of 5 µM, a 2-fold dilution series from 5 µM (2.5, 1.3, 0.63, 0.31, 0.16, and 0.08 µM), and 0. The WST-1 cell proliferation assay was performed 72 hours after the culture. For N-89, the results at concentrations of up to 6.3 µM are shown.

As a result of the measurement, the $CC_{50}$ values of N-89 and N-251 were calculated to be 9.3 µM and 3.8 µM, respectively (FIG. 10).

Taken together, the results showed that the SI value of N-89 was 22 and the SI value of N-251 was 3.9.

A slightly low $EC_{50}$ value of N-89 was obtained, and in contrast, a slightly high $EC_{50}$ value of N-251 was obtained in the 1B-4R cells as compared to the OR6 cells. A low $CC_{50}$ value of N-251 was also obtained. Thus, the SI values of N-89 and N-251 were high and low values as compared to the OR6 cells, respectively.

Example 10

Anti-HCV Activities of N-89 and N-251 in KAH5RL Assay System

Through the use of cells in which a full-length HCV genome autonomously replicates, derived from the HCV-KAH5 strain different from the HCV-O strain (KAH5RL cells), the anti-HCV activities of N-89 and N-251 were examined and the $EC_{50}$ values were calculated. An experimental scale and schedule are the same as those in Example 1.

N-89 was added so as to achieve concentrations of 10 µM, a 2-fold dilution series from 10 µM (5, 2.5, 1.3, 0.63, 0.31, and 0.16 µM), and 0. The luciferase activities were measured 72 hours after the culture.

N-251 was added so as to achieve concentrations of 5 µM, a 2-fold dilution series from 5 µM (2.5, 1.3, 0.63, 0.31, 0.16, and 0.08 µM), and 0. The luciferase activities were measured 72 hours after the culture.

Figure 11:
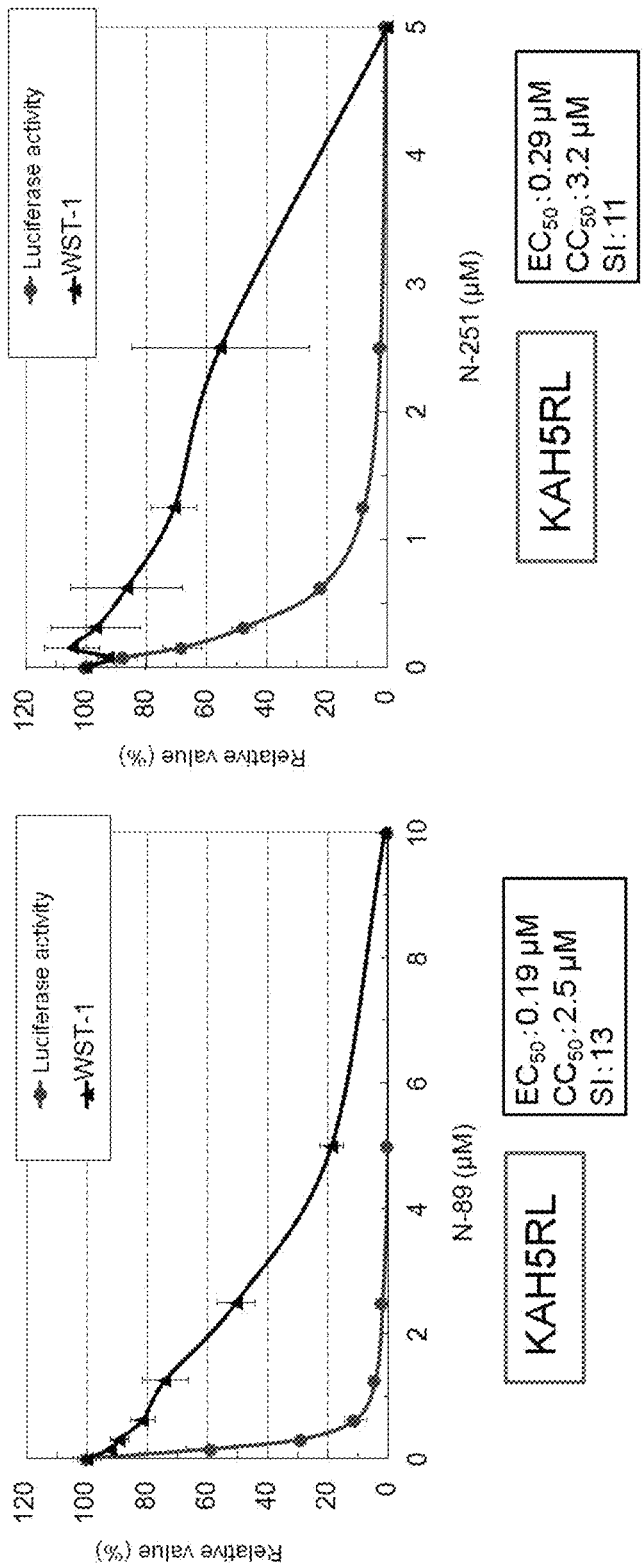
FIG. 11 shows the anti-HCV activities of N-89 and N-251 in KAH5RL cells (Example 10).

As a result of the measurement, the $EC_{50}$ values of N-89 and N-251 were calculated to be 0.19 µM and 0.29 µM, respectively (FIG. 11).

The cytotoxic effects of N-89 and N-251 were examined using KAH5RL cells and the $CC_{50}$ values were calculated. An experimental scale and schedule are the same as those in Example 1.

The concentrations of N-89 and N-251 were the same as the concentrations used for the measurement of the luciferase activity, and the WST-1 cell proliferation assay was performed 72 hours after the addition.

As a result of the measurement, the $CC_{50}$ values of N-89 and N-251 were calculated to be 2.5 µM and 3.2 µM, respectively (FIG. 11).

Taken together, the results showed that the SI value of N-89 was 13 and the SI value of N-251 was 11.

The values of N-89 and N-251 were both about 2- to 3-fold higher in the KAH5RL cells than in the ORL8 cells. The $CC_{50}$ value of N-89 was comparable and the $CC_{50}$ value of N-251 was about 2.5-fold higher. As a result, the SI values were lower than those in the ORL8 cells but were numerical values of 10 or more.

Example 11

Anti-HCV Activities of N-89 and N-251 in 1B-4RL Cells

Through the use of cells in which a full-length HCV genome autonomously replicates, derived from the HCV-1B-4 strain different from the HCV-O strain (1B-4RL cells), the anti-HCV activities of N-89 and N-251 were examined and the $EC_{50}$ values were calculated. An experimental scale and schedule are the same as those in Example 1.

N-89 and N-251 both were added so as to achieve concentrations of 5 µM, a 2-fold dilution series from 5 µM (2.5, 1.3, 0.63, 0.31, 0.16, and 0.08 µM), and 0. The luciferase activities were measured 72 hours after the culture. For N-251, the results at concentrations of up to 1.3 µM are shown.

Figure 12:
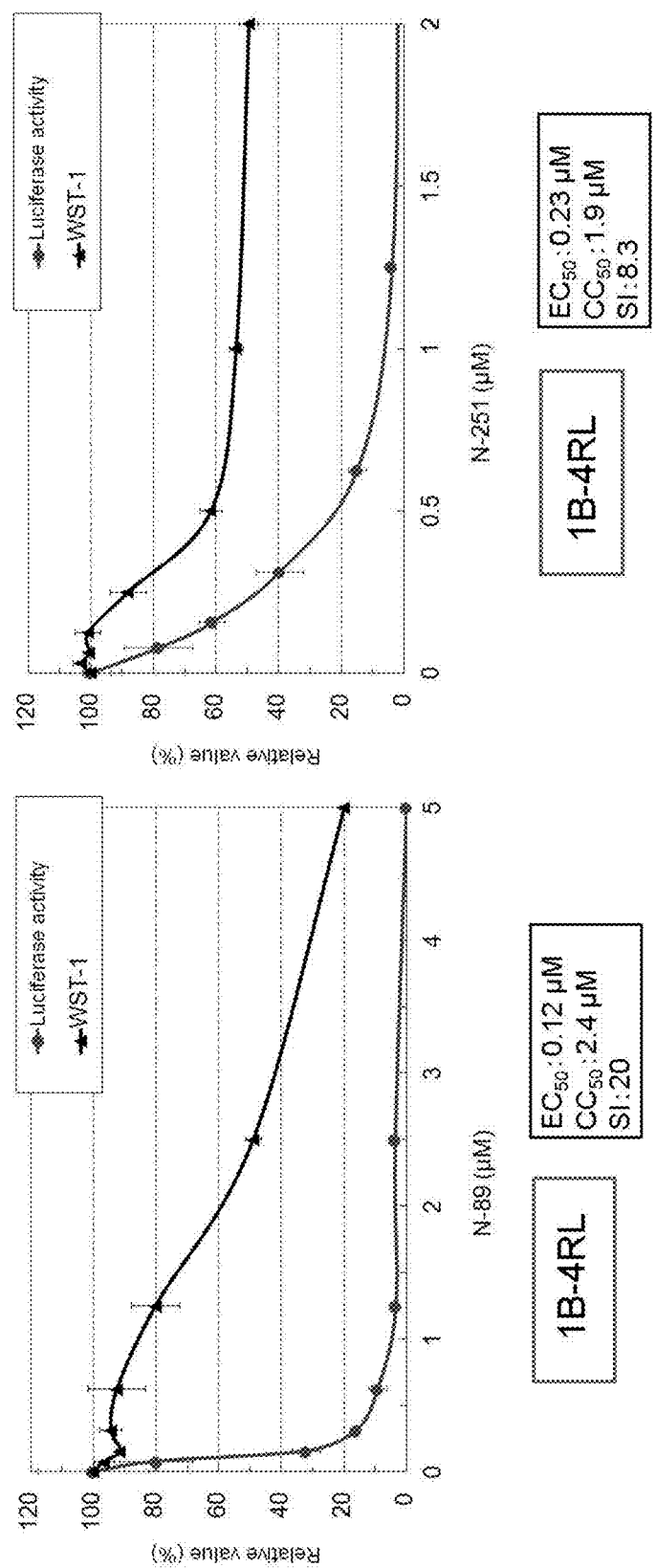
FIG. 12 shows the anti-HCV activities of N-89 and N-251 in 1B-4RL cells (Example 11).

As a result of the measurement, the $EC_{50}$ values of N-89 and N-251 were calculated to be 0.12 µM and 0.23 µM, respectively (FIG. 12).

The cytotoxic effects of N-89 and N-251 were examined using the 1B-4RL cells and the $CC_{50}$ values were calculated. An experimental scale and schedule are the same as those in Example 1.

N-89 was added at the concentrations used for the measurement of the luciferase activity, and N-251 was added so as to achieve concentrations of 2 µM, a 2-fold dilution series from 2 µM (1, 0.5, 0.25, 0.13, 0.06, and 0.03 µM), and 0. The WST-1 cell proliferation assay was performed 72 hours after the addition.

As a result of the measurement, the $CC_{50}$ values of N-89 and N-251 were calculated to be 2.4 µM and 1.9 µM, respectively (FIG. 12).

Taken together, the results showed that the SI value of N-89 was 20 and the SI value of N-251 was 8.3.

The $EC_{50}$ values of N-89 and N-251 were about 1.3-fold and 2.3-fold higher in the 1B-4RL cells than those in the ORL8 cells, respectively. The $CC_{50}$ values were both comparable to those in the ORL8 cells. Therefore, the SI values were numerical values about half as high as those in the ORL8 assay system.

Reference Example 2

Anti-HCV Activities of N-89 and N-251 on Various HCV Strains

The $EC_{50}$ values and $CC_{50}$ values of N-89 and N-251 measured in the cells derived from various HCV strains obtained in Example 1 to Example 11, and the calculated SI values were summarized in Table 1 below.

1 µM or less irrespective of HCV strains having genetic diversity and cell lines having different genetic backgrounds. Accordingly, the compounds were considered to be very promising anti-HCV agent candidates.

Example 12

Confirmation of Influences of N-89 and N-251 on HCV-RNA Replication in HCV-O/RLGE Cells HCV-O/RLGE cells (Ikeda et al., Liver Int 31:871-880, 2011) were plated onto a 6-well plate ($5 \times 10^4$ cells in 3 mL of medium for HuH-7 cell line per well) and cultured. After 24 hours, N-89 was added so as to achieve concentrations of 20 µM, a 2-fold dilution series from 20 µM (10, 5, 2.5, 1.3, 0.63, and 0.31 µM), and 0, or N-251 was added so as to achieve concentrations of 10 µM, a 2-fold dilution series from 10 µM (5, 2.5, 1.3, 0.63, 0.31, and 0.15 µM), and 0. 72 hours after the culture, the cells were lysed with 100 µL of 2×SDS buffer to prepare a sample for Western blot analysis. The Western blot analysis using an antibody against an HCV core protein (CP11; Institute of Immunology, Tokyo) was performed according to a conventional method. β-Actin was detected with an anti-β-actin antibody (AC-15; Sigma-Aldrich) in a sample diluted 10-fold with 2×SDS buffer.

Figure 13:
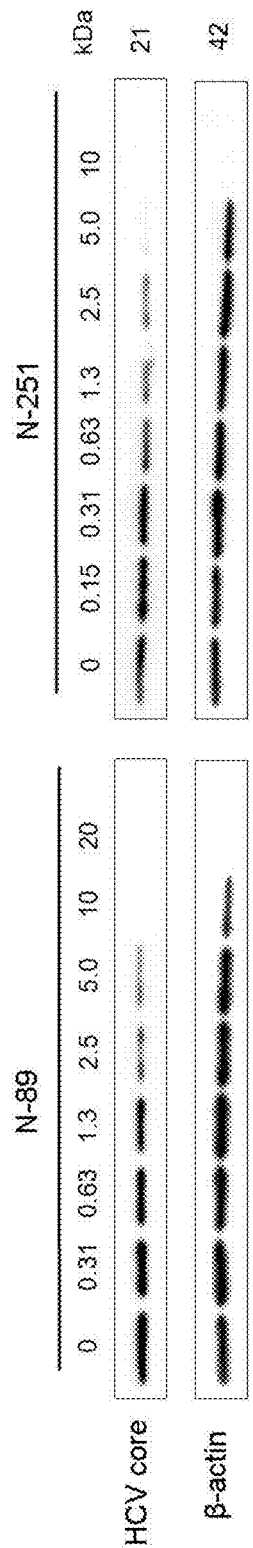
FIG. 13 shows the results of confirmation of the influences of N-89 and N-251 on HCV-RNA replication in HCV-O/RLGE cells (Example 12).

The results of the Western blot analysis (FIG. 13) showed that both of N-89 and N-251 clearly reduced the amount of an HCV core protein in a concentration region in which the amount of β-actin did not reduce. Accordingly, it was found that the anti-HCV activities of N-89 and N-251 were not due to the suppression of an internal ribosomal entry site from encephalomyocarditis virus (EMCV-IRES) but were due to the direct suppression of HCV-RNA replication.

Example 13

Production of Cured Cells from ORL8 Cells by Treatment with N-89

Based on the fact that N-89 and N-251 were found to potently suppress HCV-RNA replication, and suppressed the

TABLE 1

| | Kind of cell | | | | | | | | | | | | | |
|---|---|---|---|---|---|---|---|---|---|---|---|---|---|---|
| | HuH-7 | | | | | | | | Li23 | | | | | |
| | | | | | HCV strain | | | | | | | | | |
| | O | | 1B-4 | | AH1 | | O | | O | | 1B-4 | | KAH5 | |
| Cell | OR6 | | 1B-4R | | AH1R | | ORL8 | | ORL11 | | 1B-4RL | | KAH5RL | |
| N89 | 9.0 | 14 | 9.3 | 22 | about 0.5 | about 20 | 2.3 | 26 | 0.56 | 12 | 2.4 | 20 | 2.5 | 13 |
| | 0.66 | | 0.42 | | 0.025 | | 0.089 | | 0.045 | | 0.12 | | 0.19 | |
| N-251 | 3.0 | 4.4 | 3.8 | 3.9 | 0.49 | 3.5 | 1.3 | 13 | 1.1 | 19 | 1.9 | 8.3 | 3.2 | 11 |
| | 0.69 | | 0.98 | | 0.14 | | 0.10 | | 0.059 | | 0.23 | | 0.29 | |
| $CC_{50}$ (µM) | | SI | | | | | | | | | | | | |
| $EC_{50}$ (µM) | | | | | | | | | | | | | | |

The $EC_{50}$ values of N-89 and N-251 were from 0.025 to 0.66 µM and from 0.059 to 0.98 µM, respectively. The $CC_{50}$ values were also from 0.5 to 9.3 µM and from 0.49 to 3.8 µM, respectively. Thus, there was a tendency that N-89 had slightly more potent anti-HCV activity.

The SI values of N-89 and N-251 were from 12 to 26 and from 3.5 to 19, respectively.

The results revealed that each of N-89 and N-251 alone exhibited potent anti-HCV activity at a low concentration of level of HCV-RNA replication by 99% at a concentration of 1 µM not exhibiting cytotoxicity in the ORL8 cells, the inventors of the present invention estimated that HCV RNA was able to be completely eliminated from full-length HCV-RNA-replicating cells with the drug alone like IFN.

In order to demonstrate this point, studies were made on whether or not cured cells (cells from which HCV RNA was eliminated) were able to be produced from the ORL8 cells by treatment with N-89. A drug treatment method for the cells was performed according to a method with IFN-γ (1,000 IU/mL) (Abe K et al., Virus Res. 125:88-97, 2007) generally used in the production of cured cells by the inventors of the present invention.

$4 \times 10^5$ ORL8 cells were plated onto a 10-cm plate (10 mL of medium in the absence of G418) (Day 1), and N-89 was added so as to achieve a final concentration of 1 μM the next day (Day 2). After 3 days (Day 5), the cells were diluted 10-fold, and N-89 was added again the next day. This operation was repeated an additional four times (N-89 was added six times in total: Days 2, 6, 10, 14, 18, and 22). At the time of the dilution of the cells (Day 13), which was performed 3 days after the third addition of N-89, the cells were divided into two plates with medium in the presence of G418 (neomycin) (0.3 mg/mL) and medium in the absence of G418. Then, N-89 was added three times, a plurality of plates were prepared at the time of the final dilution of the cells, and finally, one of the plates for each of the media was subjected to CBB staining (Day 26). It should be noted that the cells were treated with N-89 at a final concentration of 1 μM, the concentration not exhibiting cytotoxicity in the WST-1 assay (FIG. 14a, the concentration indicated by the arrow)

Figure 14:
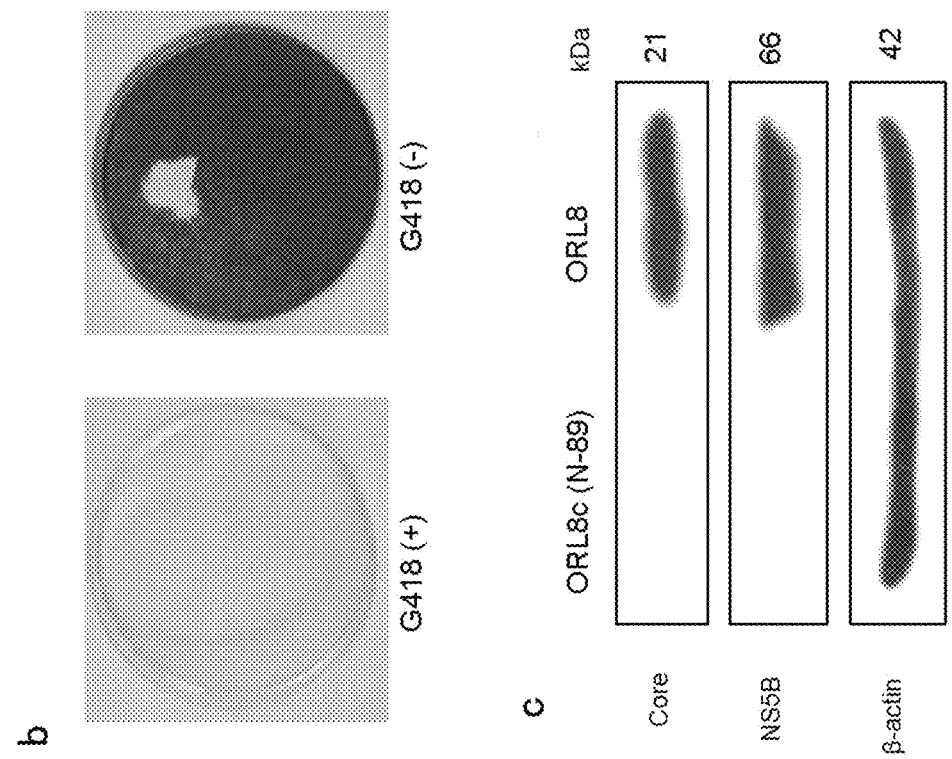
FIG. 14 show the results of production of cured cells from ORL8 cells by treatment with N-89 (Example 13).
Figure 14:
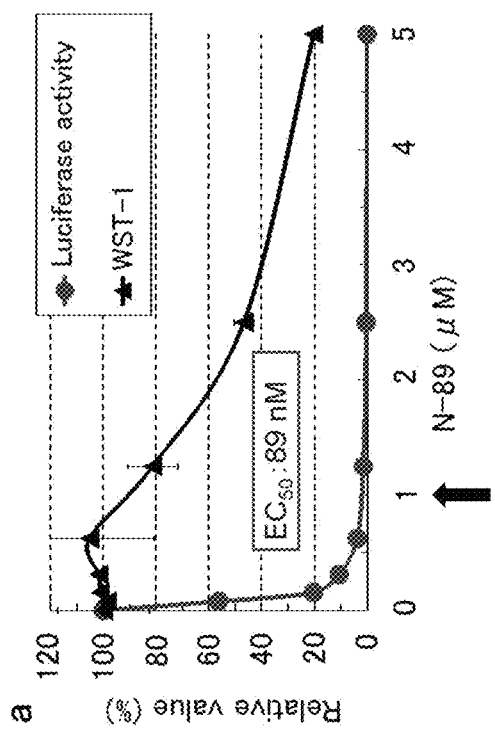

FIG. 14 show the results. FIG. 14a shows the results of the luciferase activity and the WST-1 assay, and FIG. 14b shows the results of the CBB staining. The ORL8 cells cultured in the medium in the presence of G418 were all killed, whereas the ORL8 cells cultured in the absence of G418 became confluent at a normal proliferation rate. In order to confirm that HCV RNA was eliminated from the cells, Western blot analysis was performed using an anti-HCV core antibody and an anti-HCV NS5B antibody (FIG. 14c). The ORL8 cells were used as a positive control. As a result, none of a core protein and NS5B was detected in the N-89-treated ORL8 cells (expressed as ORL8c (N-89) in FIG. 14). Accordingly, it was found that cured cells were able to be produced from the ORL8 cells by the treatment with N-89.

Further, cells obtained by subculturing HCV-O strain-derived full-length HCV-genome-replicating cells (OL8 cells and OL11 cells) (Kato et al., Virus Res. 146:41-50, 2009) for 3 years (the cells had acquired the status of genetic diversity (called quasispecies) owing to various mutations in an HCV genome caused by the sustained replication of the HCV genome) were used and similarly treated with N-89. As a result, as in the case of the ORL8 cells, cured cells were able to be produced from the OL8 cells and OL11 cells subcultured for 3 years as well.

There was no previous report that cured cells were able to be easily produced with a drug other than IFN. Therefore, in this point as well, it was revealed that the anti-HCV activity of N-89 was very potent and resistant colonies did not easily emerge.

Example 14

Effect of Antioxidant on Anti-HCV Activity of N-89 in ORL8 Cells

The effect of addition of vitamin E on the anti-HCV activity of N-89 was examined using ORL8 cells. An experimental scale and schedule are the same as those in Example 1.

N-89 and vitamin E were simultaneously added so that the concentrations of N-89 and vitamin E were set to 0.5 μM and 10 μM, respectively. The luciferase activity was measured 72 hours after the culture.

Figure 15:
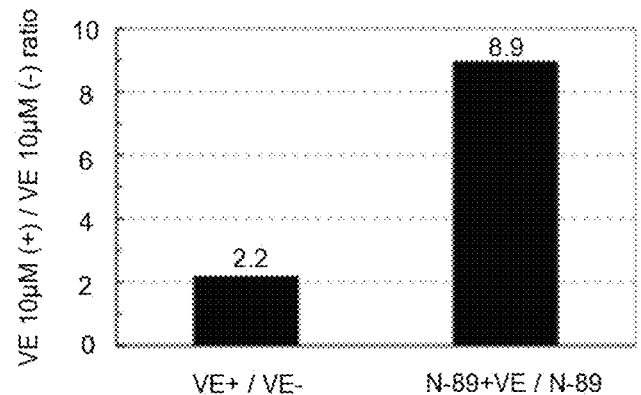
FIG. 15 shows the results of confirmation of the effect of an antioxidant on the anti-HCV activity of N-89 in ORL8 cells (Example 14).
Figure 15:
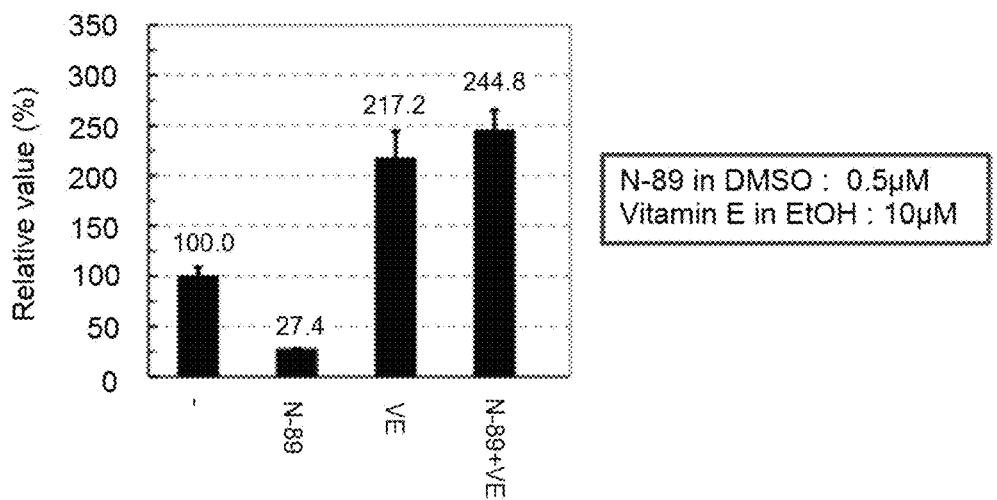

The lower panel of FIG. 15 shows the measurement results. The addition of N-89 alone reduced the HCV activity to 27%. In contrast, in the case of adding the antioxidant vitamin E alone, the luciferase activity was as high as 217%. Also in the case of using N-89 in combination with vitamin E, the luciferase activity was as high as 245%. Thus, it was found that the anti-HCV activity of N-89 was completely canceled by vitamin E.

The upper panel of FIG. 15 quantitatively shows such canceling effect. The panel was created by calculating values obtained by dividing the luciferase activities obtained in the case of adding vitamin E by the luciferase activities obtained in the case of adding no vitamin E. An indicator of a difference based on the presence or absence of vitamin E in combination with N-89 was 8.9, which was a higher value than a value of 2.2 in vitamin E alone.

The anti-HCV activity of N-89 is completely canceled by vitamin E, and hence the anti-HCV activity of N-89 is considered to be due to oxidative stress, unlike artemisinin.

Example 15

Effect of Antioxidant on Anti-HCV Activity of N-251 in ORL8 Cells

The effect of addition of vitamin E on the anti-HCV activity of N-251 was examined using ORL8 cells. An experimental scale and schedule are the same as those in Example 1.

N-251 and vitamin E were simultaneously added so that the concentrations of N-251 and vitamin E were set to 0.5 μM and 10 μM, respectively. The luciferase activity was measured 72 hours after the culture.

Figure 16:
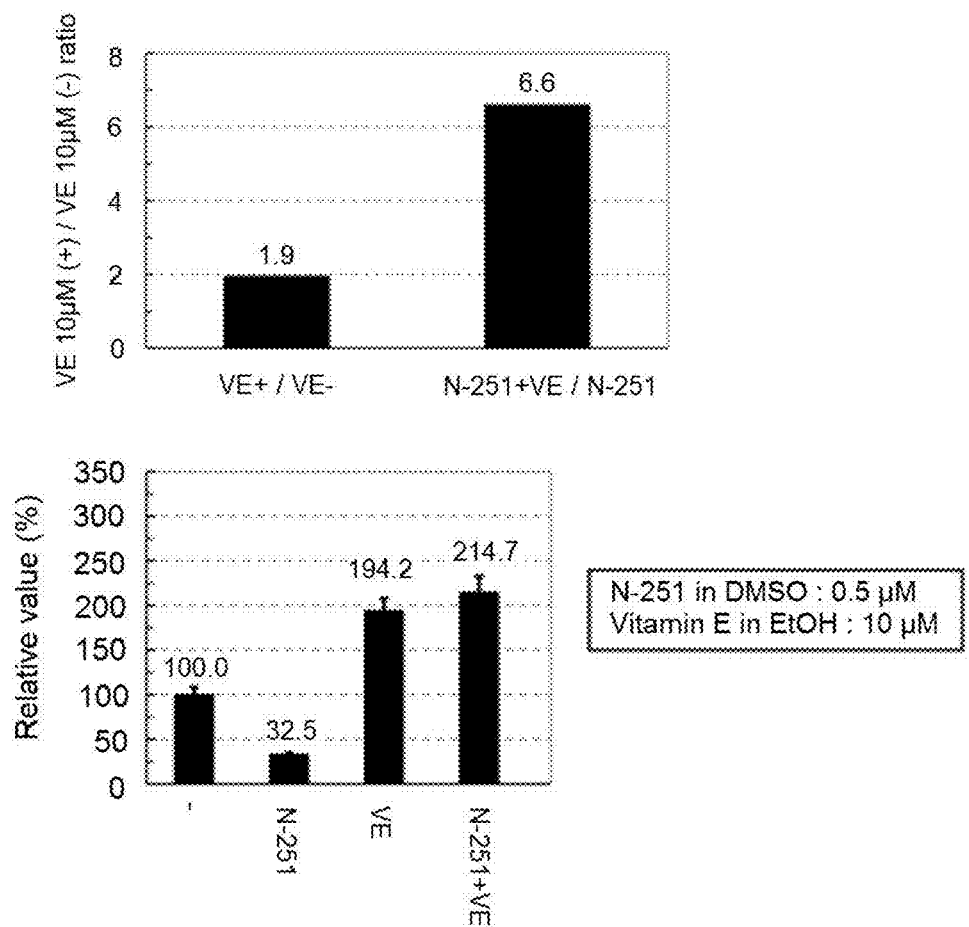
FIG. 16 shows the results of confirmation of the effect of an antioxidant on the anti-HCV activity of N-251 in ORL8 cells (Example 15).

The lower panel of FIG. 16 shows the measurement results. The addition of N-251 alone reduced the HCV activity to 33%. In contrast, in the case of adding the antioxidant vitamin E alone, the luciferase activity was as high as 194%. Also in the case of using N-251 in combination with vitamin E, the luciferase activity was as high as 215%. Thus, it was found that the anti-HCV activity of N-251 was completely canceled by vitamin E.

As shown in the upper panel of FIG. 15, the canceling effect is quantitatively shown in the upper panel of FIG. 16. An indicator of a difference based on the presence or absence of vitamin E in combination with N-251 was 6.6, which was a higher value than a value of 1.9 in vitamin E alone.

The anti-HCV activity of N-251 is completely canceled by vitamin E, and hence the anti-HCV activity of N-251 is also considered to be due to oxidative stress.

Example 16

Confirmation of Influences of Oxidizing Agents on Anti-HCV Activity of N-89 in ORL8 Cells The effects of addition of $KNO_3$ and $NaClO_4$ on the anti-HCV activity of N-89 were examined using ORL8 cells. An experimental scale and schedule are the same as those in Example 1.

N-89 and $KNO_3$ or $NaClO_4$ were simultaneously added so that the concentrations of N-89 and $KNO_3$ or $NaClO_4$ were set to 0.5 μM and 10 μM, respectively. The luciferase activity was measured 72 hours after the culture.

Figure 17:
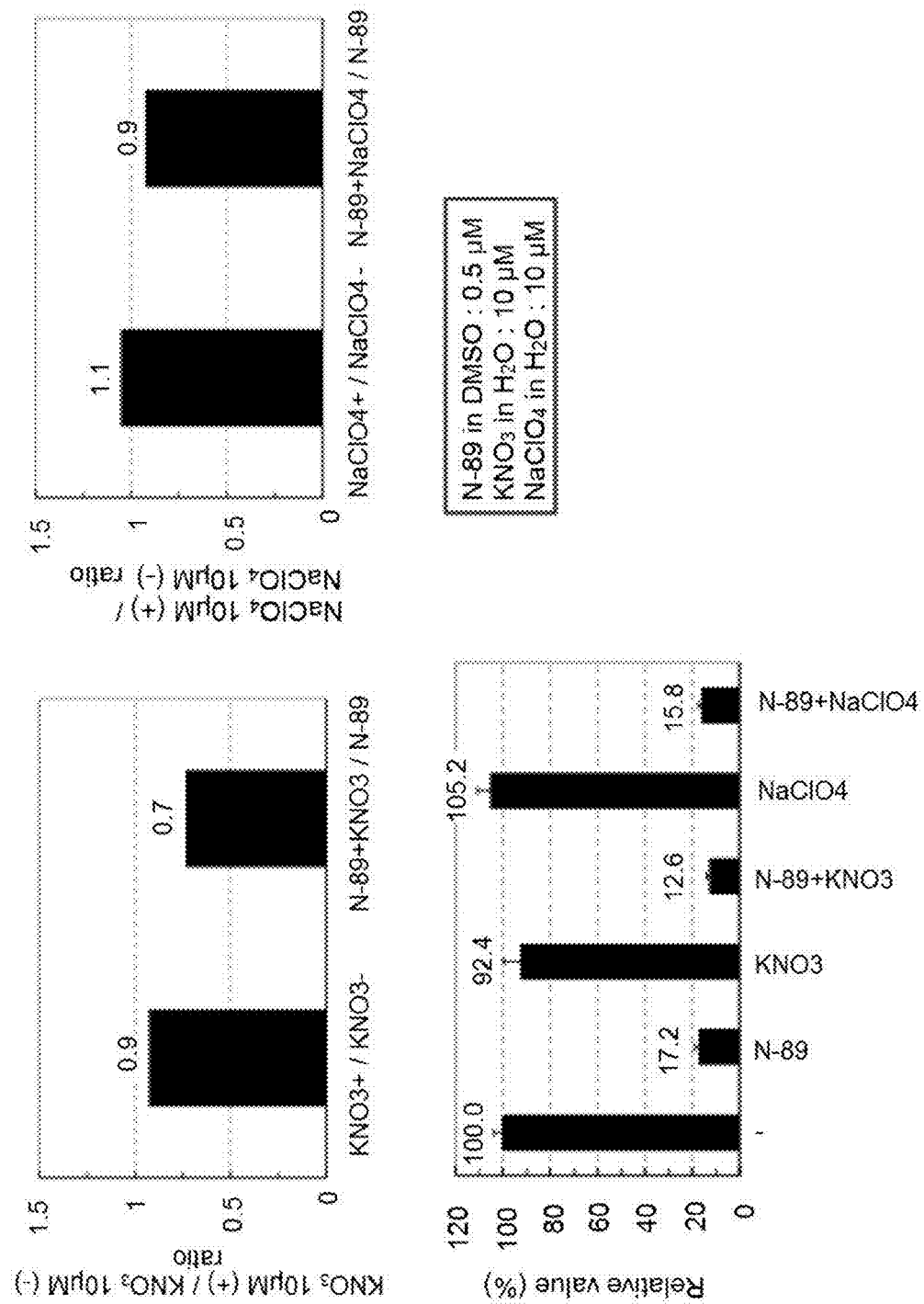
FIG. 17 shows the results of confirmation of the influences of oxidizing agents on the anti-HCV activity of N-89 in ORL8 cells (Example 16).

FIG. 17 shows the results. Even the addition of $KNO_3$ or $NaClO_4$ caused no change in luciferase activity, and $KNO_3$ or $NaClO_4$ in combination with N-89 had no influence on the anti-HCV activity. Accordingly, it is considered that the anti-HCV activity of N-89 is due to oxidative stress, but is not due to such an oxidative effect as exhibited by the oxidizing agent such as $KNO_3$ or $NaClO_4$.

Comparative Example 2

Effect of Antioxidant on Anti-HCV Activity of Artemisinin in ORL8 Cells

The effect of addition of vitamin E on the anti-HCV activity of artemisinin was examined using ORL8 cells. An experimental scale and schedule are the same as those in Example 1.

Cyclosporine (CsA), which had been known to undergo the canceling of the anti-HCV activity by the addition of the antioxidant vitamin E, and IFN-α, which had been known to undergo no canceling, were also used as controls.

Artemisinin and vitamin E were simultaneously added so that the concentrations of artemisinin and vitamin E were set to 100 μM and 10 μM, respectively. The luciferase activity was measured 72 hours after the culture. The same experiments as in artemisinin were performed so that the concentrations of CsA and IFN-α were set to 0.4 μg/mL and 1 IU/mL, respectively.

Figure 18:
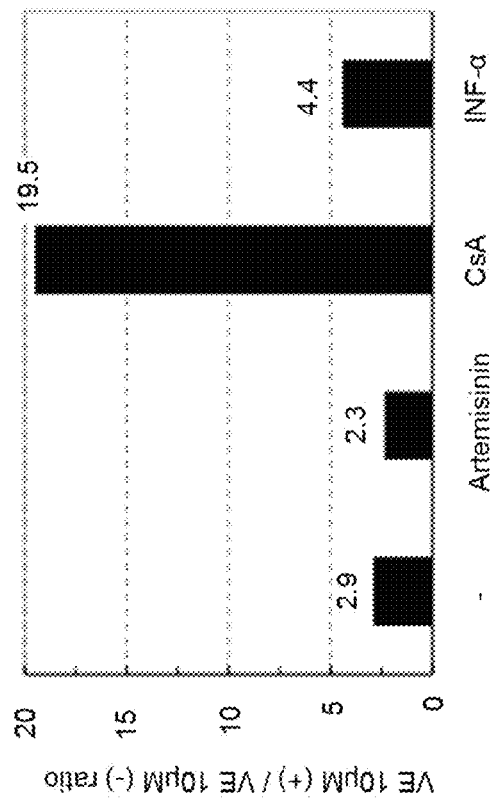
FIG. 18 shows the results of confirmation of the effect of an antioxidant on the anti-HCV activity of artemisinin in ORL8 cells (Comparative Example 2).
Figure 18:
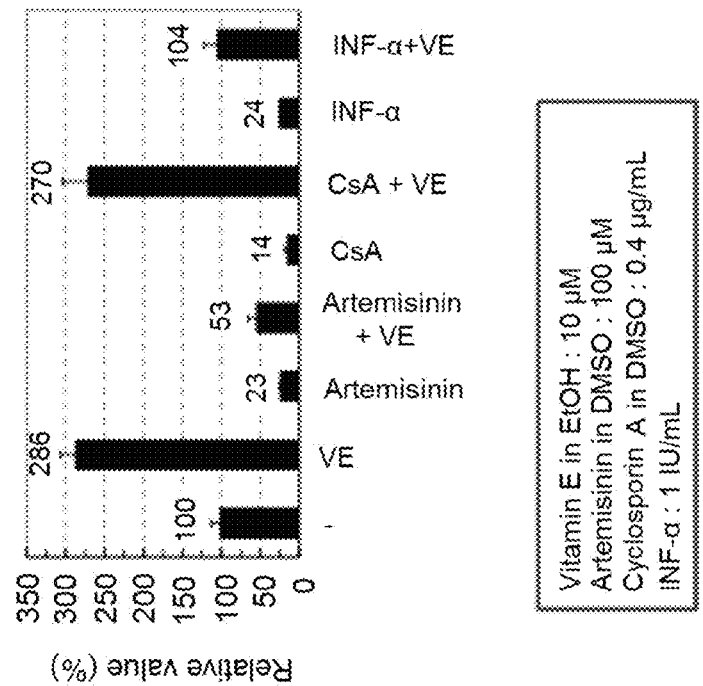

The left panel of FIG. 18 shows the measurement results. The luciferase activity increased about 3-fold and the level of HCV RNA increased in the case of adding vitamin E alone. The luciferase activity reduced to 23% in artemisinin alone. The luciferase activity increased to 53% in the case of using artemisinin in combination with vitamin E. The luciferase activity reduced to 14% in CsA alone, whereas the luciferase activity markedly increased to 270% in the case of using CsA in combination vitamin E, indicating that the anti-HCV activity of CsA was completely canceled. However, the canceling effect by the addition of vitamin E was slightly found in IFN-α in this experiment, but was not comparable to that of CsA.

As shown in the upper panel of FIG. 15, the right panel of FIG. 18 quantitatively shows the canceling effect. As a result, a value of 2.9 was obtained in the case of using no anti-HCV agent. Values of 2.3 and 4.4 were obtained in artemisinin and IFN-α, respectively. In contrast to those results, a high value of 19.5 was obtained in CsA. The anti-HCV activity of CsA is completely canceled by vitamin E, and hence the anti-HCV activity of CsA is considered to be due to oxidative stress. However, the anti-HCV activity of artemisinin is not canceled by vitamin E, and hence the molecular mechanism of the anti-HCV activity of artemisinin is considered to be different from the oxidative stress. Accordingly, the molecular mechanisms of the anti-HCV activities of N-89 and N-251 are considered to be different from that of artemisinin. The canceling effects of vitamin E on the anti-HCV activities of CsA and IFN-α have already been reported (Yano M et al., Antimicrob. Agents Chemother. 51:2016-2027, 2007).

Example 17

Effect of N-89 in Combination with RBV in ORL8 Cells

The effect of N-89 in combination with RBV was examined using ORL8 cells. An experimental scale and schedule are the same as those in Example 1.

The drugs RBV and N-89 were added so that the concentrations of RBV were set to 0, 12.5, 25, and 50 μM and the concentrations of N-89 were set to 0, 0.1, 0.2, and 0.4 μM at each concentration of RBV. The luciferase activity was measured 72 hours after the culture.

Figure 19:
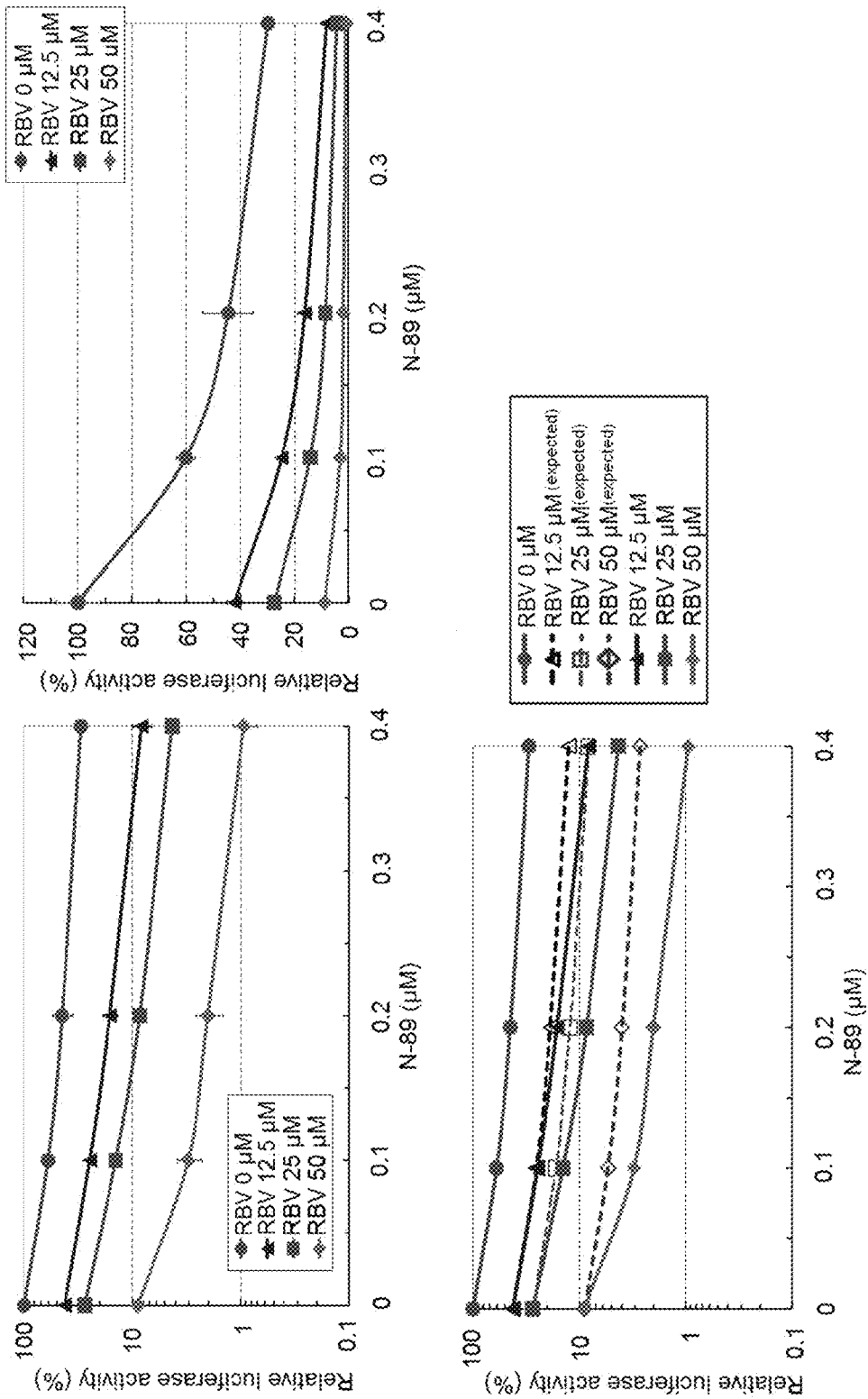
FIG. 19 shows the results of confirmation of the effect of N-89 in combination with RBV in ORL8 cells (Example 17).

The upper left panel of FIG. 19 and the upper right panel of FIG. 19 show the logarithmic and linear plots expressed by % of the measurement results, respectively. The lower left panel of FIG. 19 shows the logarithmic plots of an effect curve (expected) expected as an additive effect in comparison with actual measurement results.

In the cases of using N-89 in combination with RBV at 12.5, 25, and 50 μM, the actually measured values were found to be much lower than the expected additive curve. The $CC_{50}$ value of N-89 in the ORL8 cells is 2.3 μM (Example 3), and hence its influence is considered to be small. Accordingly, it was found that N-89 in combination with RBV provided a synergistic effect in the ORL8 cells.

Example 18

Effect of N-251 in Combination with RBV in ORL8 Cells

The effect of N-251 in combination with RBV was examined using ORL8 cells. An experimental scale and schedule are the same as those in Example 1.

The drugs RBV and N-89 were added so that the concentrations of RBV were set to 0, 12.5, 25, and 50 μM and the concentrations of N-89 were set to 0, 0.1, 0.2, and 0.4 μM at each concentration of RBV. The luciferase activity was measured 72 hours after the culture.

Figure 20:
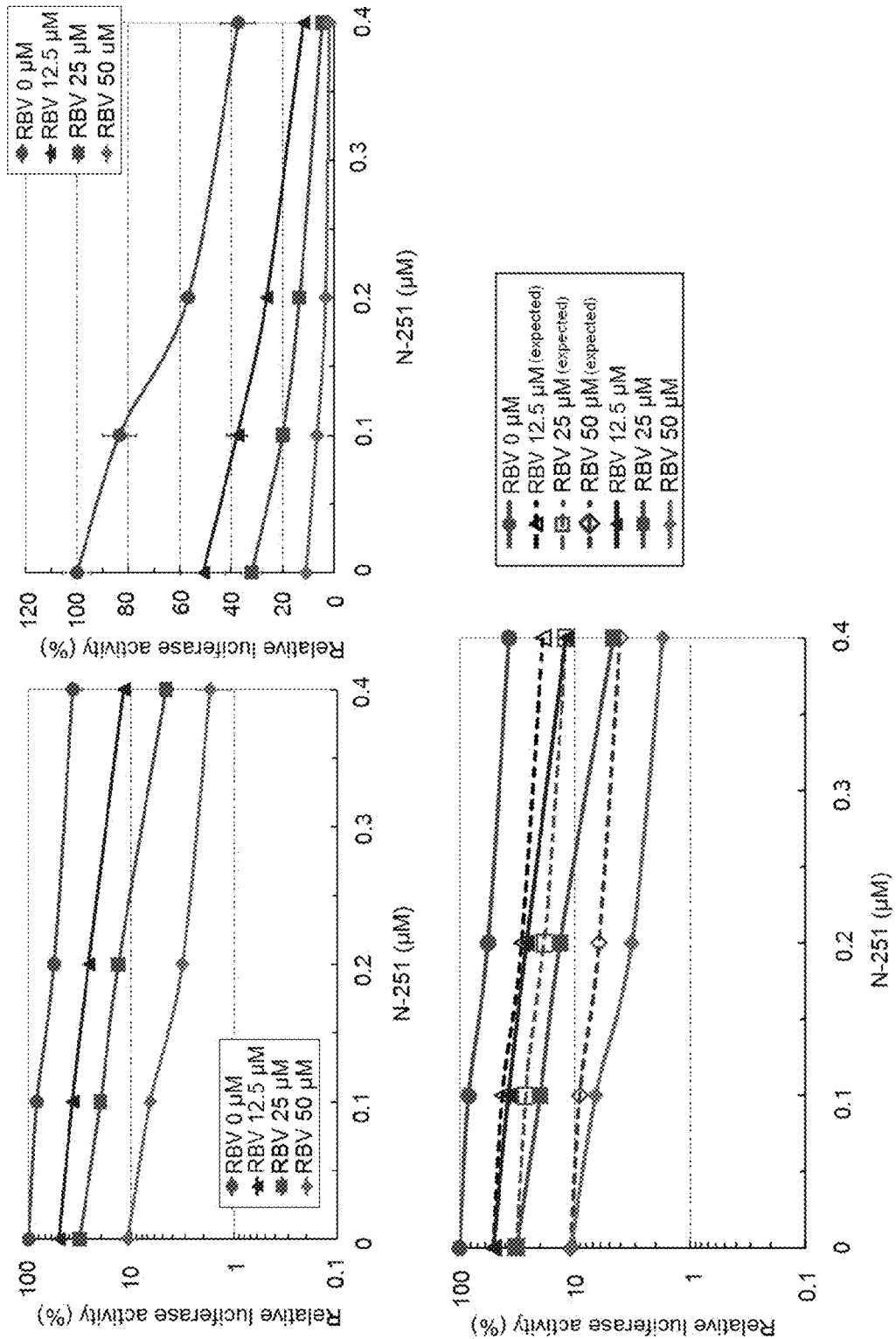
FIG. 20 shows the results of confirmation of the effect of N-251 in combination with RBV in ORL8 cells (Example 18).

The upper left panel of FIG. 20 and the upper right panel of FIG. 20 show the logarithmic and linear plots expressed by % of the measurement results, respectively. The lower left panel of FIG. 20 shows the logarithmic plots of an effect curve (expected) expected as an additive effect in comparison with actual measurement results.

In the cases of using N-251 in combination with RBV at 12.5, 25, and 50 μM, the actually measured values were found to be much lower than the expected additive curve. The $CC_{50}$ value of N-251 in the ORL8 cells is 1.3 μM (Example 3), and hence its influence is considered to be small. Accordingly, it was found that N-251 in combination with RBV provided a synergistic effect in the ORL8 cells.

Example 19

Effect of N-89 in Combination with IFN-α and RBV in ORL8 Cells

The effect of N-89 in combination with IFN-α and RBV was examined using ORL8 cells. An experimental scale and schedule are the same as those in Example 1.

The drugs N-89, IFN-α, and RBV were added so that the concentrations of the two drugs IFN-α and RBV were fixed as follows: both of IFN-α and RBV at 0; IFN-α at 1 IU/mL and RBV at 6.25 μM; IFN-α at 4 IU/mL and RBV at 12.5 μM; and IFN-α at 16 IU/mL and RBV at 25 μM, and the concentrations of N-89 were set to 0, 0.1, 0.2, and 0.4 μM in the respective combinations of IFN-α and RBV. The luciferase activity was measured 72 hours after the culture.

Figure 21:
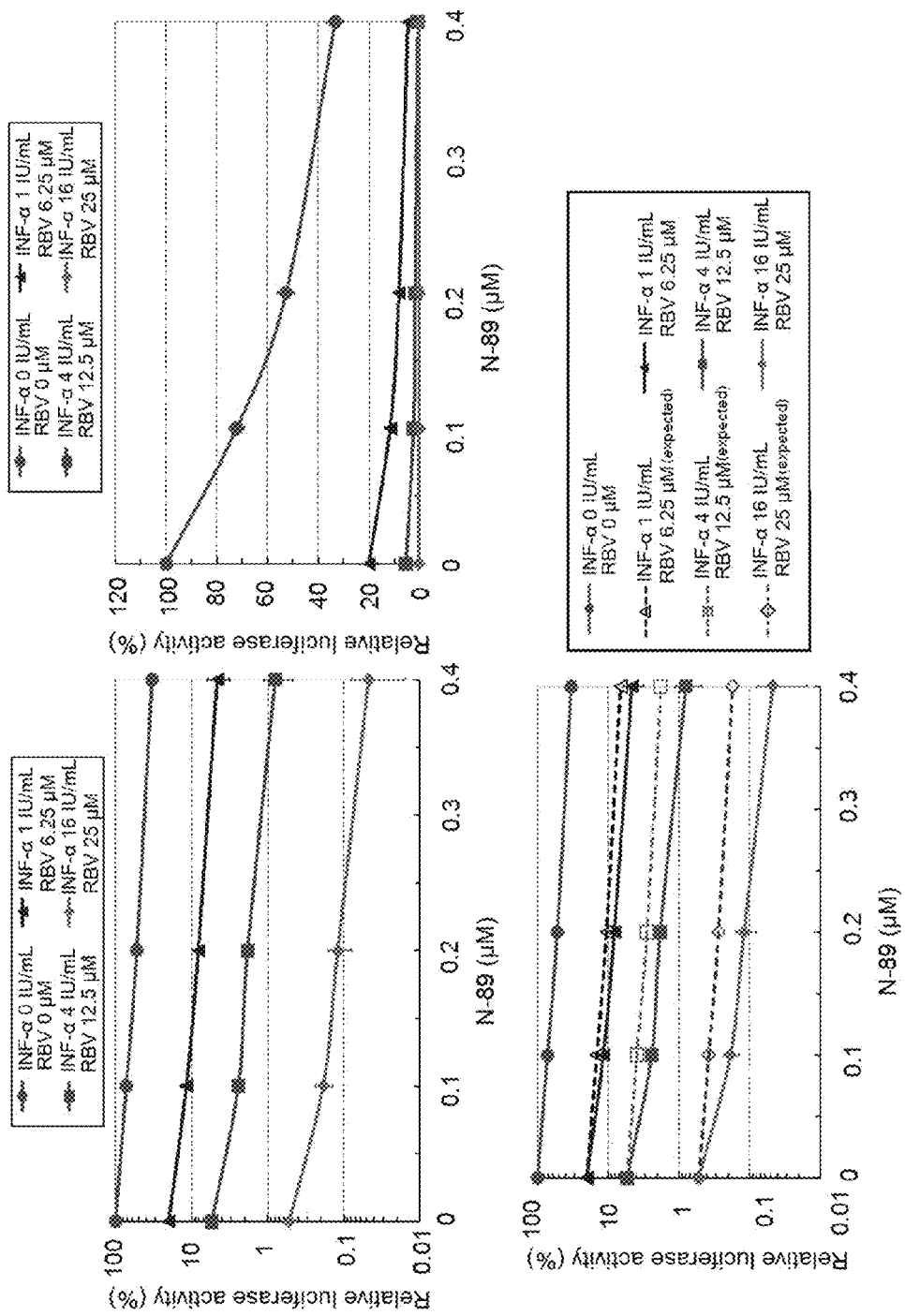
FIG. 21 shows the results of confirmation of the effect of N-89 in combination with IFN-α and RBV in ORL8 cells (Example 19).

The upper left panel of FIG. 21 and the upper right panel of FIG. 21 show the logarithmic and linear plots expressed by % of the measurement results, respectively. The lower left panel of FIG. 21 shows the logarithmic plots of an effect curve (expected) expected as an additive effect in comparison with actual measurement results.

It was found that there were little gaps between the actually measured values by the addition of N-89 and values expected as an additive effect in the case of IFN-α at 1 IU/mL and RBV at 6.25 μM, whereas the actually measured values by the addition of N-89 were much lower than values expected as an additive effect in the case of IFN-α at 4 IU/mL and RBV at 12.5 μM and the case of IFN-α at 16 IU/mL and RBV at 25

μM. The $CC_{50}$ value of N-89 in the ORL8 cells is 2.3 μM (Example 3), and hence its influence is considered to be small. Accordingly, it was found that N-89 in combination with IFN-α and RBV provided a synergistic effect in the ORL8 cells.

Example 20

Effect of N-89 in Combination with CsA in ORL8 Cells

The effect of N-89 in combination with CsA was examined using ORL8 cells. An experimental scale and schedule are the same as those in Example 1.

The drugs CsA and N-89 were added so that the concentrations of CsA were set to 0.2, 0.3, and 0.4 μM and the concentrations of N-89 were set to 0, 0.1, 0.2, and 0.4 μM at each concentration of CsA. The luciferase activity was measured 72 hours after the culture.

Figure 22:
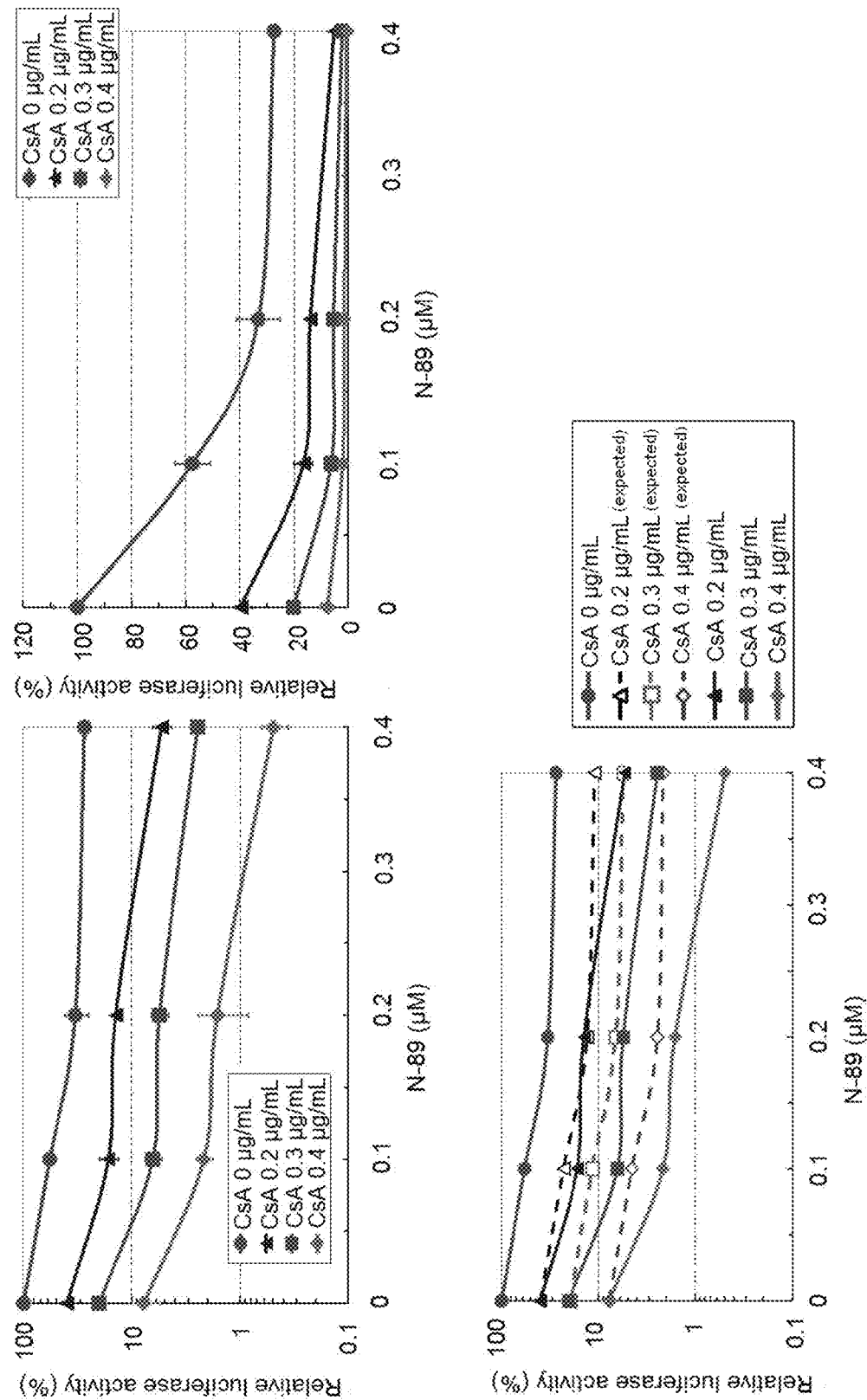
FIG. 22 shows the results of confirmation of the effect of N-89 in combination with CsA in ORL8 cells (Example 20).

The upper left panel of FIG. 22 and the upper right panel of FIG. 22 show the logarithmic and linear plots expressed by % of the measurement results, respectively. The lower left panel of FIG. 22 shows the logarithmic plots of an effect curve (expected) expected as an additive effect in comparison with actual measurement results.

In the cases of using N-89 in combination with CsA at 0.2, 0.3, and 0.4 μM, the actually measured values were found to be much lower than the expected additive curve. The $CC_{50}$ value of N-89 in the ORL8 cells is 2.3 μM (Example 3) and the $CC_{50}$ value of CsA is 3.2 μM, and hence its influence is considered to be small. Accordingly, it was found that N-89 in combination with CsA provided a synergistic effect in the ORL8 cells.

Example 21

Effect of N-251 in Combination with CsA in ORL8 Cells

The effect of N-251 in combination with CsA was examined using ORL8 cells. An experimental scale and schedule are the same as those in Example 1.

The drugs CsA and N-251 were added so that the concentrations of CsA were set to 0.2, 0.3, and 0.4 μM and the concentrations of N-251 were set to 0, 0.1, 0.2, and 0.4 μM at each concentration of CsA. The luciferase activity was measured 72 hours after the culture.

Figure 23:
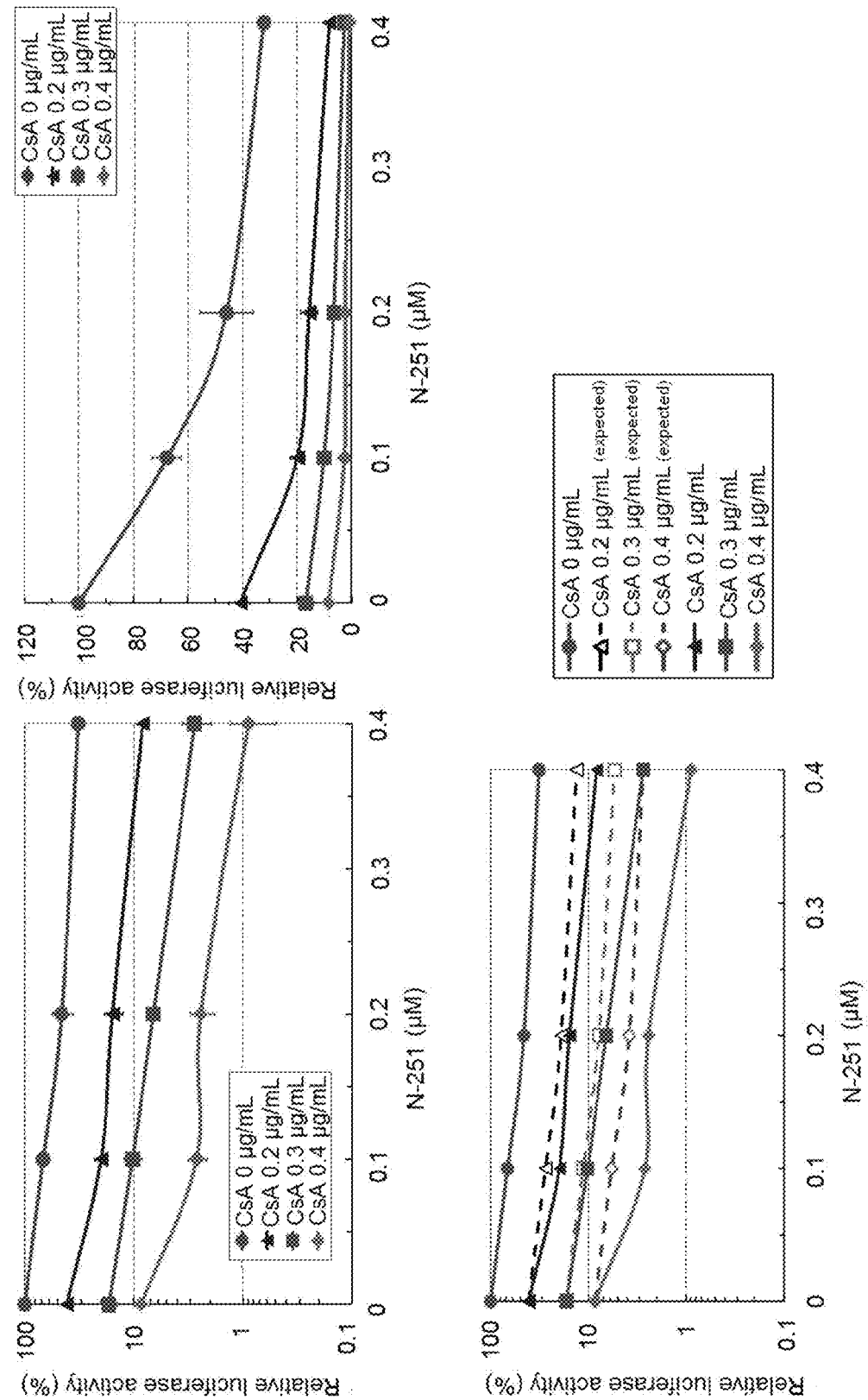
FIG. 23 shows the results of confirmation of the effect of N-251 in combination with CsA in ORL8 cells (Example 21).

The upper left panel of FIG. 23 and the upper right panel of FIG. 23 show the logarithmic and linear plots expressed by % of the measurement results, respectively. The lower left panel of FIG. 23 shows the logarithmic plots of an effect curve (expected) expected as an additive effect in comparison with actual measurement results.

In the cases of using N-251 in combination with CsA at 0.2, 0.3, and 0.4 μM, the actually measured values were found to be much lower than the expected additive curve. The $CC_{50}$ value of N-251 in the ORL8 cells is 1.3 μM (Example 3) and the $CC_{50}$ value of CsA is 3.2 μM, and hence its influence is considered to be small. Accordingly, it was found that N-251 in combination with CsA provided a synergistic effect in the ORL8 cells.

Example 22

Effect of N-89 in Combination with Fluvastatin (FLV) in ORL8 Cells

The effect of N-89 in combination with FLV was examined using ORL8 cells. An experimental scale and schedule are the same as those in Example 1.

The drugs FLV and N-89 were added so that the concentrations of FLV were set to 0.3, 1.0, and 3.0 μM and the concentrations of N-89 were set to 0, 0.1, 0.2, and 0.4 μM at each concentration of FLV. The luciferase activity was measured 72 hours after the culture.

Figure 24:
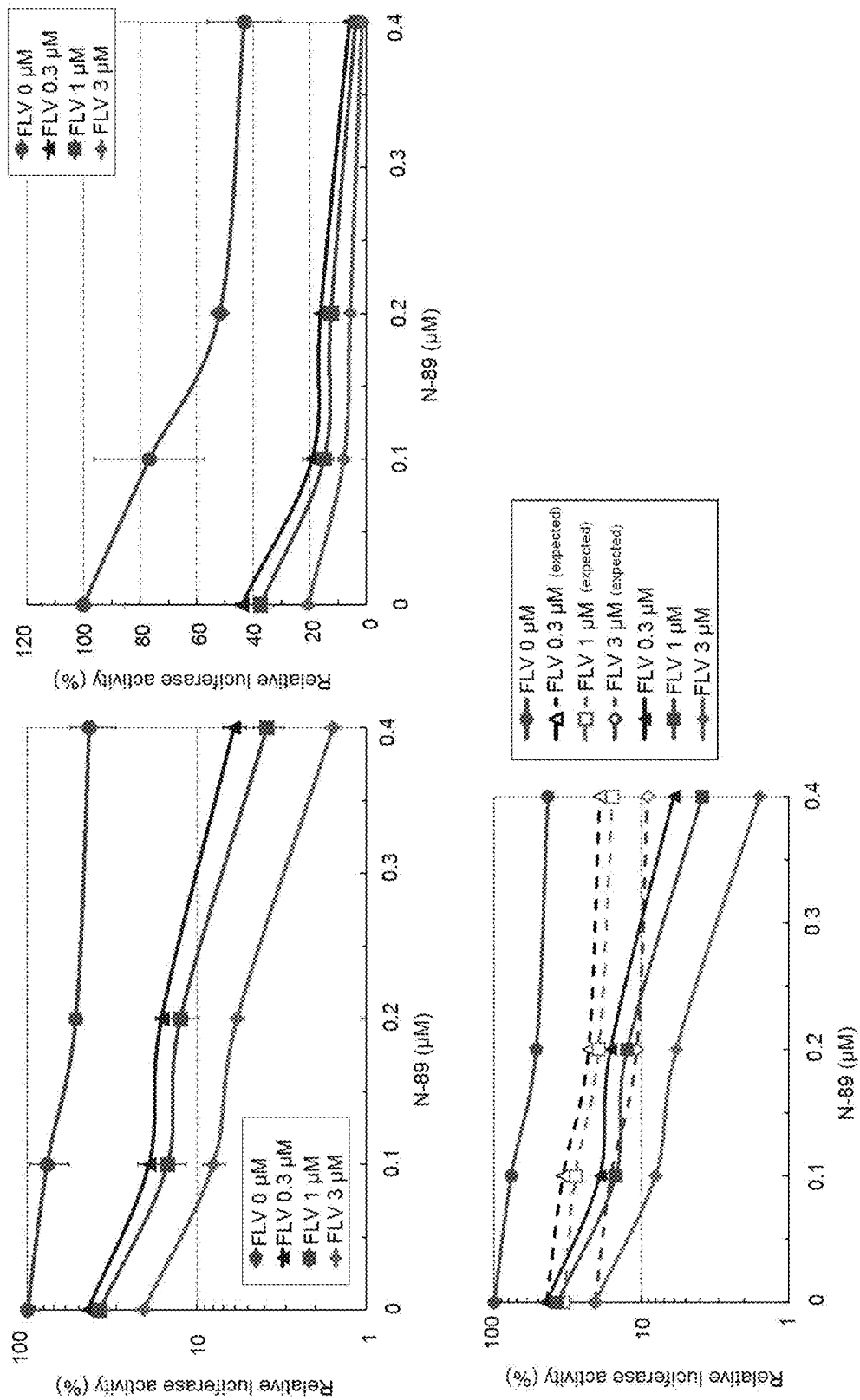
FIG. 24 shows the results of confirmation of the effect of N-89 in combination with FLV in ORL8 cells (Example 22).

The upper left panel of FIG. 24 and the upper right panel of FIG. 24 show the logarithmic and linear plots expressed by % of the measurement results, respectively. The lower left panel of FIG. 24 shows the logarithmic plots of an effect curve (expected) expected as an additive effect in comparison with actual measurement results.

In the cases of using N-89 in combination with FLV at 0.3, 1.0, and 3.0 μM, the actually measured values were found to be much lower than the expected additive curve. The $CC_{50}$ value of N-89 in the ORL8 cells is 2.3 μM (Example 3) and the $CC_{50}$ value of FLV is 21 μM, and hence its influence is considered to be small. Accordingly, it was found that N-89 in combination with FLV provided a synergistic effect in the ORL8 cells.

Example 23

Effect of N-251 in Combination with FLV in ORL8 Cells

The effect of N-251 in combination with FLV was examined using ORL8 cells. An experimental scale and schedule are the same as those in Example 1.

The drugs FLV and N-251 were added so that the concentrations of FLV were set to 0.3, 1.0, and 3.0 μM and the concentrations of N-251 were set to 0, 0.1, 0.2, and 0.4 μM at each concentration of FLV. The luciferase activity was measured 72 hours after the culture.

Figure 25:
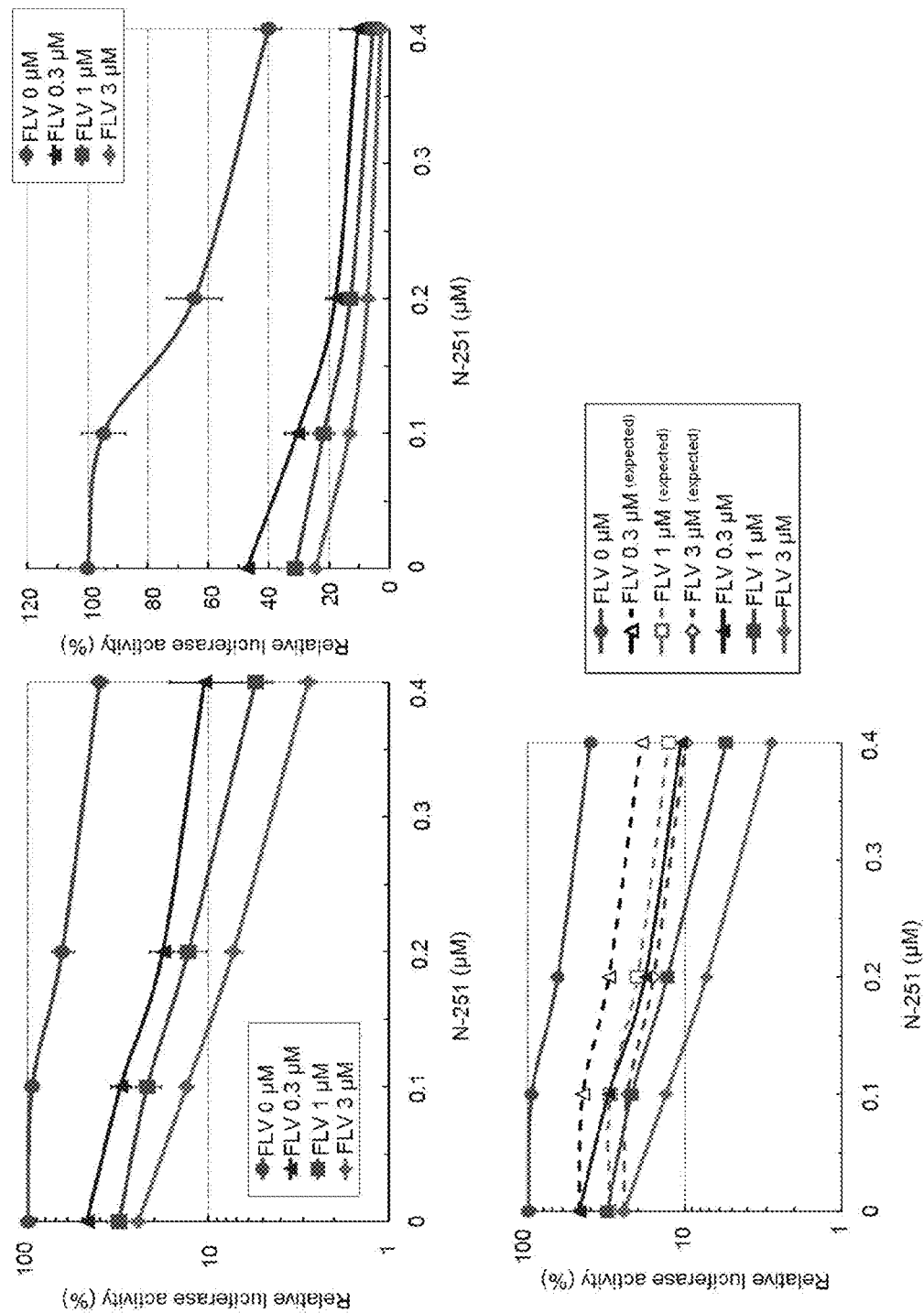
FIG. 25 shows the results of confirmation of the effect of N-251 in combination with FLV in ORL8 cells (Example 23).

The upper left panel of FIG. 25 and the upper right panel of FIG. 25 show the logarithmic and linear plots expressed by % of the measurement results, respectively. The lower left panel of FIG. 25 shows the logarithmic plots of an effect curve (expected) expected as an additive effect in comparison with actual measurement results.

In the cases of using N-251 in combination with FLV at 0.3, 1.0, and 3.0 μM, the actually measured values were found to be much lower than the expected additive curve. The $CC_{50}$ value of N-251 in the ORL8 cells is 1.3 μM (Example 3) and the $CC_{50}$ value of FLV is 21 μM, and hence its influence is considered to be small. Accordingly, it was found that N-251 in combination with FLV provided a synergistic effect in the ORL8 cells.

INDUSTRIAL APPLICABILITY

As described in detail above, the novel anti-HCV agent of the present invention has been comprehensively assessed using cells derived from a plurality of HCV strains and cell lines. Therefore, the novel anti-HCV agent is considered to exhibit a potent anti-HCV action by itself even in different HCV strains and cell lines, and thus is very useful. In addition, according to the novel anti-HCV agent of the present invention, HCV-RNA-replicating cells from which HCV RNA had been completely eliminated, i.e., cured cells were able to be obtained. Accordingly, the use of the novel anti-HCV agent of the present invention can be highly expected to remarkably increase a therapeutic effect on hepatitis C and markedly improve a curing ratio. In addition, the anti-HCV agent of the present invention is considered to have low cytotoxicity and high safety, and not to be influenced by the genetic diversity and mutations of HCV, and hence is very useful. Further, the anti-HCV agent of the present invention, when used in combination with the existing anti-HCV agent (e.g., IFN, RBV, CsA, or FLV), exhibits a synergistic effect of anti-HCV activities, and hence is also useful for the current therapy with IFN in combination with RBV. The administration of IFN or RBV exhibits a side effect, and hence the anti-HCV agent of the present invention in combination with IFN or RBV can reduce the dosage of IFN or RBV and can also alleviate the side effect.

The invention claimed is:

1. A method for preventing or treating hepatitis C, comprising administering to a subject in need thereof a composition comprising as an active ingredient a peroxide derivative represented by the general formula (I):

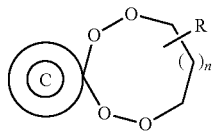

Formula (I)

wherein C represents an alicyclic hydrocarbon ring group which may or may not be substituted, n represents an integer of from 1 to 6, and R represents a hydrogen atom or a hydroxyalkyl group.

2. The method according to claim 1, wherein C represents an alicyclic hydrocarbon ring group which has a lower alkyl group as a substituent.

3. The method according to claim 1, wherein C represents an alicyclic hydrocarbon ring group free of a substituent.

4. According to claim 1, wherein C represents a cyclododecylidene group free of a substituent.

5. The method according to claim 1, wherein n is 1 to 4.

6. The method according to claim 1, wherein the peroxide derivative is a compound represented by the following formula (II) or formula (III)

Formula (II)

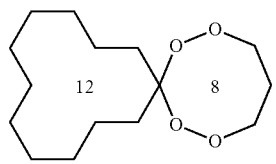

N-89

Formula (III)

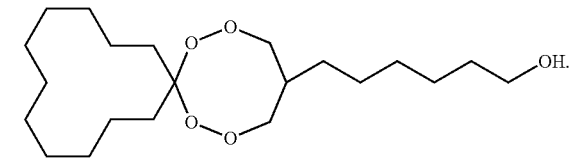

N-251

7. The method according to claim 1, comprising administering at least one additional drug selected from the group consisting of IFN (interferon), RBV (ribavirin), CsA (cyclosporine), and FLV (fluvastatin) to the subject.

8. The method according to claim 7, wherein the peroxide derivative and the additional drug is administered simultaneously or at different times.

9. A method of suppressing or inhibiting HCV (hepatitis C virus) infection, replication, particle production, or re-infection in a subject, comprising administering to a subject in need thereof a composition comprising as an active ingredient a peroxide derivative represented by the general formula (I):

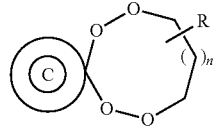

Formula (I)

wherein C represents an alicyclic hydrocarbon ring group which may or may not be substituted, n represents an integer of from 1 to 6, and R represents a hydrogen atom or a hydroxyalkyl group.

10. The method according to claim 9, comprising suppressing or inhibiting HCV (hepatitis C virus) replication.

11. The method according to claim 9, wherein C represents an alicyclic hydrocarbon ring group which has a lower alkyl group as a substituent.

12. The method according to claim 9, wherein C represents an alicyclic hydrocarbon ring group free of a substituent.

13. The method according to claim 9, wherein C represents a cyclododecylidene group free of a substituent.

14. The method according to claim 9, wherein n is 1 to 4.

15. The method according to claim 9, wherein the peroxide derivative is a compound represented by the following formula (II) or formula (III)

Formula (II)

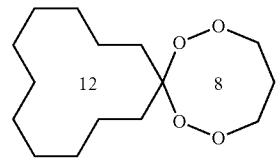

N-89

Formula (III)

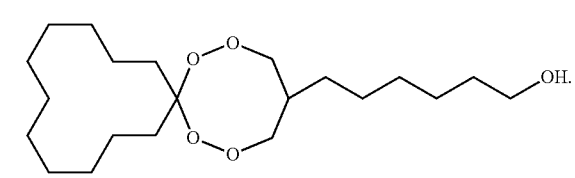

N-251

* * * * *